(12) United States Patent
Kwak et al.

(10) Patent No.: US 7,754,349 B2
(45) Date of Patent: Jul. 13, 2010

(54) SILANYLAMINE-BASED COMPOUND AND ORGANIC LIGHT-EMITTING DEVICE INCLUDING ORGANIC LAYER INCLUDING THE SILANYLAMINE-BASED COMPOUND

(75) Inventors: Yoon-Hyun Kwak, Suwon-si (KR); Seok-Hwan Hwang, Suwon-si (KR); Young-Kook Kim, Suwon-si (KR)

(73) Assignee: Samsung Mobile Display Co., Ltd., Suwon-si (KR)

( * ) Notice: Subject to any disclaimer, the term of this patent is extended or adjusted under 35 U.S.C. 154(b) by 399 days.

(21) Appl. No.: 11/947,985

(22) Filed: Nov. 30, 2007

(65) Prior Publication Data

US 2008/0171227 A1 Jul. 17, 2008

(30) Foreign Application Priority Data

Jan. 15, 2007 (KR) .................... 10-2007-0004387

(51) Int. Cl.
| | |
|---|---|
| B32B 9/00 | (2006.01) |
| C07F 7/10 | (2006.01) |
| C09K 11/06 | (2006.01) |
| H01L 51/54 | (2006.01) |

(52) U.S. Cl. .................. 428/690; 428/917; 548/406; 313/504; 313/506

(58) Field of Classification Search .................. None
See application file for complete search history.

(56) References Cited

U.S. PATENT DOCUMENTS

| | | | |
|---|---|---|---|
| 4,356,429 | A | 10/1982 | Tang |
| 6,465,115 | B2 | 10/2002 | Shi et al. |
| 6,596,415 | B2 | 7/2003 | Shi et al. |

FOREIGN PATENT DOCUMENTS

| | | |
|---|---|---|
| JP | 11-329734 | 11/1999 |
| KR | 2007-24020 | 3/2007 |

OTHER PUBLICATIONS

Adachi et al. "Endothermic Energy Transfer: A Mechanism for Generating Very Efficient High-Energy Phosphorescent Emission in Organic Materials." *Appl. Phys. Lett.*, 79, 2082-2084, 2001.

*Primary Examiner*—Dawn L Garrett
(74) *Attorney, Agent, or Firm*—Stein McEwen, LLP

(57) ABSTRACT

A silanylamine-based compound is represented by Formula 1 below. An organic light-emitting device includes an organic layer that includes the silanylamine-based compound:

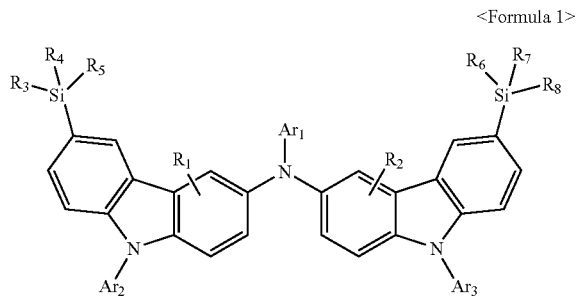

<Formula 1> wherein $R_1$, $R_2$, $R_3$, $R_4$, $R_5$, $R_6$, $R_7$, $R_8$, $Ar_1$, $Ar_2$, and $Ar_3$ are as defined in the specification. The silanylamine-based compound has good electrical characteristics and charge transport capability, and thus, is useful as a hole injection material, a hole transport material, and/or an emitting material for fluorescent or phosphorescent devices capable of producing light of a full spectrum of colors, including red, green, blue, and white. Thus, the organic light-emitting device including the organic layer including the silanylamine-based compound shows high efficiency, a low driving voltage, and high brightness.

24 Claims, 3 Drawing Sheets

| |
|---|
| Second electrode |
| Electron injection layer |
| Electron transport layer |
| Hole blocking layer |
| Emitting layer |
| Hole transport layer |
| Hole injection layer |
| First electrode |

FIG. 1

| Second electrode |
| --- |
| One or more organic layers, at least one of which contains the silanylamine-containing compound of Formula 1 |
| First electrode |

FIG. 2

| Second electrode |
| --- |
| Emitting layer |
| Hole injection layer |
| First electrode |

FIG. 3

| Second electrode |
| --- |
| Electron transport layer |
| Emitting layer |
| Hole transport layer |
| Hole injection layer |
| First electrode |

FIG. 4

| Second electrode |
| --- |
| Electron injection layer |
| Electron transport layer |
| Emitting layer |
| Hole transport layer |
| Hole injection layer |
| First electrode |

FIG. 5

| Second electrode |
| --- |
| Electron transport layer |
| Emitting layer |
| Hole injection/ hole transport layer |
| First electrode |

FIG. 6

| Second electrode |
| --- |
| Electron injection layer |
| Electron transport layer |
| Emitting layer |
| Hole injection/hole transport layer |
| First electrode |

FIG. 7

| Second electrode |
| --- |
| Electron injection layer |
| Electron transport layer |
| Hole blocking layer |
| Emitting layer |
| Hole transport layer |
| Hole injection layer |
| First electrode |

SILANYLAMINE-BASED COMPOUND AND ORGANIC LIGHT-EMITTING DEVICE INCLUDING ORGANIC LAYER INCLUDING THE SILANYLAMINE-BASED COMPOUND

CROSS-REFERENCE TO RELATED APPLICATION

This application claims the benefit of Korean Application No. 2007-4387, filed Jan. 15, 2007, in the Korean Intellectual Property Office, the disclosure of which is incorporated herein by reference.

BACKGROUND OF THE INVENTION

1. Field of the Invention

Aspects of the present invention relate to a silanylamine-based compound and an organic light-emitting device including an organic layer including the silanylamine-based compound. More particularly, aspects of the present invention relate to a silanylamine-based compound which has electrical stability, good charge transport capability, and a high glass transition temperature, and can prevent crystallization, and an organic light-emitting device including an organic layer including the silanylamine-based compound.

2. Description of the Related Art

Organic light-emitting devices are self-emitting devices that have advantages such as a wide viewing angle, good contrast, and a rapid response time. Thus, there has been an increasing interest in organic light-emitting devices. Moreover, organic light-emitting devices show good driving voltage and response speed characteristics and can create polychromatic light, and thus, extensive research into organic light-emitting devices has been conducted.

Generally, organic light-emitting devices have a stacked structure including an anode, an emitting layer, and a cathode. A hole injection layer, a hole transport layer, or an electron injection layer may be further disposed between the anode and the emitting layer or between the emitting layer and the cathode to form an anode/hole transport layer/emitting layer/cathode structure, an anode/hole transport layer/emitting layer/electron injection layer/cathode structure, or the like.

A fluorene derivative and an anthracene derivative are known as materials for forming a hole transport layer (U.S. Pat. Nos. 6,596,415 and 6,465,115).

However, organic light-emitting devices including hole transport layers formed of conventional hole transport layer materials are unsatisfactory in terms of lifetime, efficiency, and power consumption characteristics, and thus, there is room for improvement in conventional organic light-emitting devices.

SUMMARY OF THE INVENTION

Aspects of the present invention provide a material that has electrical stability, good charge transport capability, and a high glass transition temperature, can prevent crystallization, and that is suitable as an organic layer material for fluorescent or phosphorescent devices capable of producing light of a full spectrum of colors, including red, green, blue, and white, and a method of preparing the same. Aspects of the present invention also provide an organic light-emitting device showing high efficiency, a low driving voltage, and high brightness, by virtue of employing an organic layer including the material.

According to an aspect of the present invention, there is provided a silanylamine-based compound represented by Formula 1 below:

<Formula 1>

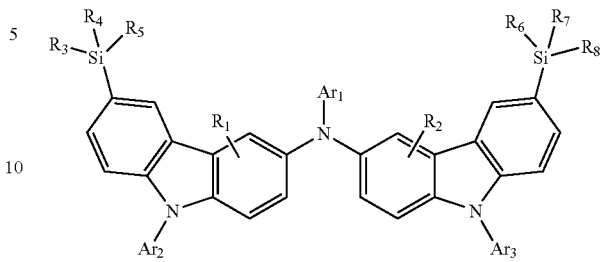

wherein, $R_1$, $R_2$, $R_3$, $R_4$, $R_5$, $R_6$, $R_7$, and $R_8$ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_6$-$C_{30}$ aryloxy group, a substituted or unsubstituted $C_6$-$C_{30}$ aryl group, or a substituted or unsubstituted $C_2$-$C_{30}$ heteroaryl group, and adjacent groups selected from $R_3$, $R_4$, $R_5$, $R_6$, $R_7$, and $R_8$ may optionally join together to form a saturated or unsaturated carbon ring; and $Ar_1$, $Ar_2$, and $Ar_3$ are each independently hydrogen, a substituted or unsubstituted $C_5$-$C_{30}$ aryl group, or a substituted or unsubstituted $C_2$-$C_{30}$ heteroaryl group.

According to another aspect of the present invention, there is provided an organic light-emitting device including a first electrode; a second electrode; and an organic layer interposed between the first electrode and the second electrode, the organic layer including the silanylamine-based compound.

An organic light-emitting device including an organic layer including a silanylamine-based compound of Formula 1 can exhibit a low driving voltage, high brightness, high efficiency, high current density, etc.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1-8 are schematic representations of organic light-emitting devices according to embodiments of the present invention.

DETAILED DESCRIPTION OF THE EMBODIMENTS

Figure 8:
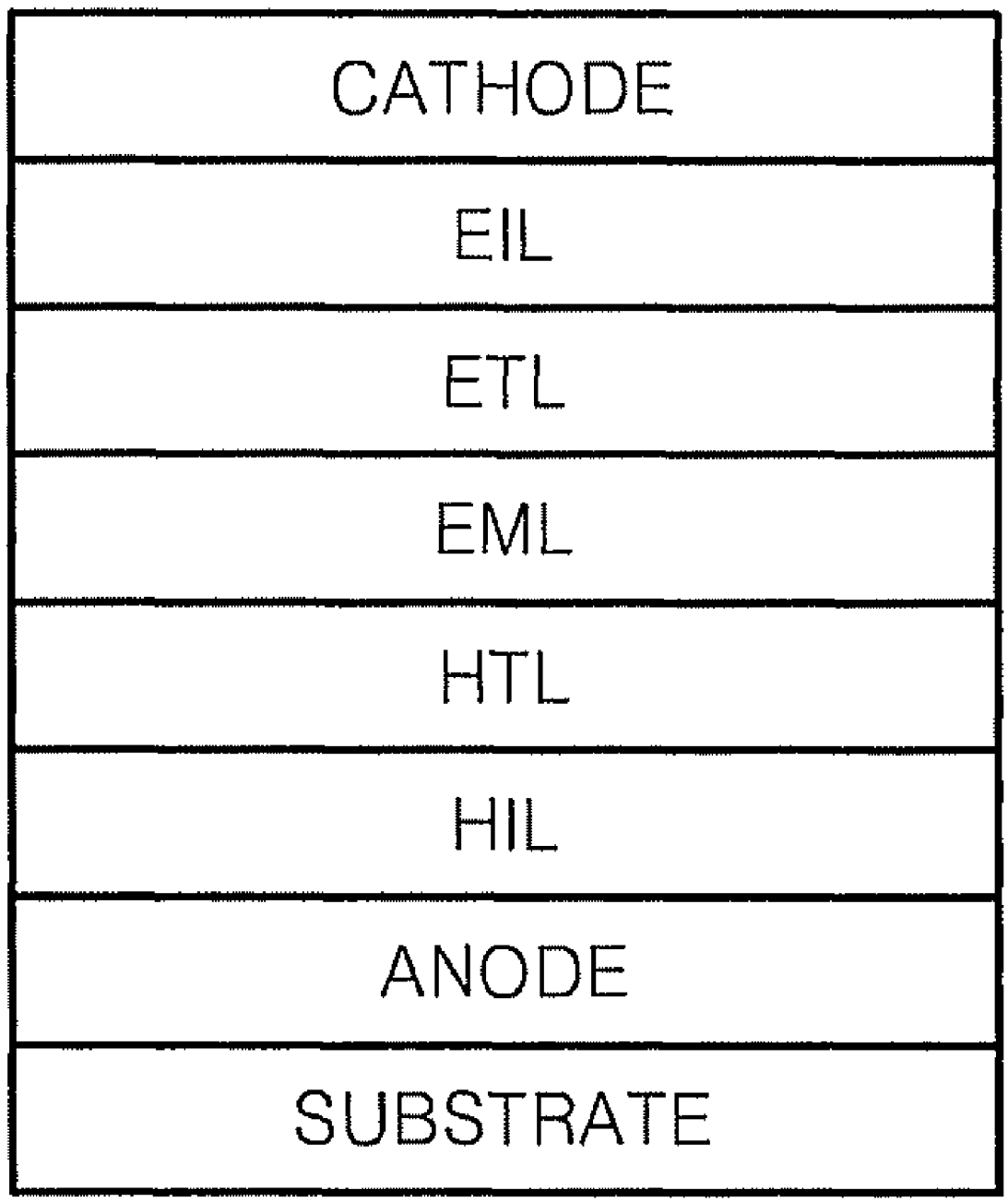

Reference will now be made in detail to the present embodiments of the present invention, examples of which are illustrated in the accompanying drawings. The embodiments are described below in order to explain the present invention by referring to the figures. It is to be understood that where is stated herein that one layer is "formed on" or "disposed on" a second layer, the first layer may be formed or disposed directly on the second layer or there may be an intervening layer between the first layer and the second layer. Further, as used herein, the term "formed on" is used with the same meaning as "located on" or "disposed on" and is not meant to be limiting regarding any particular fabrication process.

Aspects of the present invention provide a silanylamine-based compound represented by Formula 1 below:

<Formula 1>

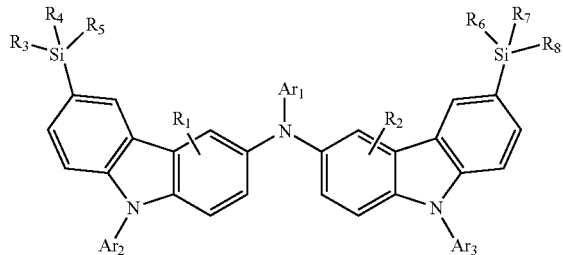

wherein,

R$_1$, R$_2$, R$_3$, R$_4$, R$_5$, R$_6$, R$_7$, and R$_8$ are each independently hydrogen, a substituted or unsubstituted C$_1$-C$_{30}$ alkyl group, a substituted or unsubstituted C$_2$-C$_{30}$ alkenyl group, a substituted or unsubstituted C$_2$-C$_{30}$ alkynyl group, a substituted or unsubstituted C$_1$-C$_{30}$ alkoxy group, a substituted or unsubstituted C$_5$-C$_{30}$ aryloxy group, a substituted or unsubstituted C$_5$-C$_{30}$ aryl group, or a substituted or unsubstituted C$_2$-C$_{30}$ heteroaryl group, and adjacent groups selected from R$_3$, R$_4$, R$_5$, R$_6$, R$_7$, and R$_8$ may optionally join together to form a saturated or unsaturated carbon ring; and Ar$_1$, Ar$_2$, and Ar$_3$ are each independently hydrogen, a substituted or unsubstituted C$_5$-C$_{30}$ aryl group, or a substituted or unsubstituted C$_2$-C$_{30}$ heteroaryl group.

The silanylamine-based compound according to aspects of the present invention is a material that has electrical stability, good charge transport capability, and a high glass transition temperature, and can prevent crystallization, and has two silane groups and two or more carbazole groups in its molecule. The silanylamine-based compound of Formula 1 is useful as a hole injection material, a hole transport material, and/or an emitting material, thereby making it possible to manufacture an organic light-emitting device with high efficiency, a low driving voltage, and high brightness.

As non-limiting examples, Ar$_1$, Ar$_2$, and Ar$_3$ may be each independently a substituted or unsubstituted C$_5$-C$_{12}$ aryl group or a substituted or unsubstituted C$_3$-C$_{15}$ heteroaryl group. As more specific, non-limiting examples, Ar$_1$, Ar$_2$, and Ar$_3$ may be a phenyl group, a C$_1$-C$_5$ alkylphenyl group, a C$_1$-C$_5$alkoxyphenyl group, a cyanophenyl group, a phenoxyphenyl group, a halophenyl group, a naphthyl group, a C$_1$-C$_5$ alkylnaphthyl group, a C$_1$-C$_5$ alkoxynaphthyl group, a cyanonaphthyl group, a halonaphthyl group, a fluorenyl group, a carbazolyl group, a C$_1$-C$_5$ alkylcarbazolyl group, a biphenyl group, a C$_1$-C$_5$ alkylbiphenyl group, a C$_1$-C$_5$ alkoxybiphenyl group, or a pyridyl group. As more specific, non-limiting examples, Ar$_1$, Ar$_2$, and Ar$_3$ may be a fluorenyl group, a carbazolyl group, a phenyl group, a naphthyl group, a biphenyl group, or an aryl group substituted with 1-3 substituents. For example, the substituents may be C$_1$-C$_3$ alkyl, C$_1$-C$_3$ alkoxy, cyano, phenoxy, phenyl, halogen, etc.

As more specific, non-limiting examples, Ar$_1$, Ar$_2$, and Ar$_3$ may be a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, or p-tolyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinolyl group, a phenanthryl group, a triphenylene group, a pentaphenyl group, a hexaphenyl group, a carbazolyl group, etc.

As the molecular weight of the compound of Formula 1 increases, deposition of the compound may become difficult. Thus, as non-limiting example, R$_1$, R$_2$, R$_3$, R$_4$, R$_5$, R$_6$, R$_7$, and R$_8$ may be each independently a substituted or unsubstituted C$_1$-C$_{10}$ alkyl group, a substituted or unsubstituted C$_1$-C$_{10}$ alkoxy group, a substituted or unsubstituted C$_6$-C$_{12}$ aryl group, a substituted or unsubstituted C$_6$-C$_{12}$ aryloxy group, or a C$_3$-C$_{12}$ heteroaryl group. As more specific, non-limiting examples, R$_1$, R$_2$, R$_3$, R$_4$, R$_5$, R$_6$, R$_7$, and R$_8$ may be each independently a C$_1$-C$_{10}$ alkyl group, a phenyl group, a halophenyl group, a cyanophenyl group, a C$_1$-C$_{10}$ alkylphenyl group, a C$_1$-C$_{10}$ alkoxyphenyl group, a biphenyl group, a halobiphenyl group, a naphthyl group, a halonaphthyl group, a C$_1$-C$_{10}$ alkylnaphthyl group, or a C$_1$-C$_{10}$ alkoxynaphthyl group.

Examples of an unsubstituted C1-C20 alkyl group used in the compound of Formula 1 include methyl, ethyl, propyl, isobutyl, sec-butyl, pentyl, iso-amyl, and hexyl. At least one hydrogen atom of the alkyl group may be substituted by a halogen atom, a hydroxy group, a nitro group, a cyano group, an amino group, an amidino group, hydrazine, hydrazone, a carboxyl group or its salt, a sulfonyl group or its salt, a phosphonyl group or its salt, a C1-C30 alkyl group, a C1-C30 alkenyl group, a C1-C30 alkynyl group, a C6-C30 aryl group, a C7-C30 arylalkyl group, a C2-C20 heteroaryl group, or a C3-C30 heteroarylalkyl group.

Examples of an unsubstituted C1-C20 alkoxy group used in the compound of Formula 1 include methoxy, ethoxy, phenyloxy, cyclohexyloxy, naphthyloxy, isopropyloxy, and diphenyloxy. At least one hydrogen atom of the alkoxy group may be substituted by the same substituents as those recited in the above definition of the alkyl group.

The term "unsubstituted C6-C20 aryl group" used herein refers to an aromatic carbocyclic system containing one or more rings. The unsubstituted C6-C20 aryl group may be used alone or in combination. The rings may be attached to each other as a pendant group or may be fused. At least one hydrogen atom of the aryl group may be substituted by the same substituents as those recited in the above definition of the alkyl group.

The aryl group may be a phenyl group, an ethylphenyl group, an ethylbiphenyl group, o-, m-, and p-fluorophenyl groups, a dichlorophenyl group, a dicyanophenyl group, a trifluoromethoxyphenyl group, o-, m-, and p-tolyl groups, o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a methylnaphthyl group, an anthracenyl group, an azulenyl group, a heptalenyl group, an acenaphthylenyl group, a phenalenyl group, a fluorenyl group, an, anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a carbazolyl group, etc.

Examples of an unsubstituted aryloxy group used in the compound of Formula 1 include phenyloxy, naphthyleneoxy, and diphenyloxy. At least one hydrogen atom of the aryloxy group may be substituted by the same substituents as those recited in the above definition of the alkyl group.

The term "unsubstituted heteroaryl group" used herein refers to a monovalent monocyclic or bicyclic aromatic organic compound of 6-30 carbon atoms containing one, two or three heteroatoms selected from N, O, P, and S. At least one hydrogen atom of the heteroaryl group may be substituted by the same substituents as those recited in the above definition of the alkyl group.

Examples of the heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, etc.

Examples of the arylamine-based compound of Formula 1 include, but not limited to, compounds 1-60 represented in Formula 2 below:

<Formula 2>

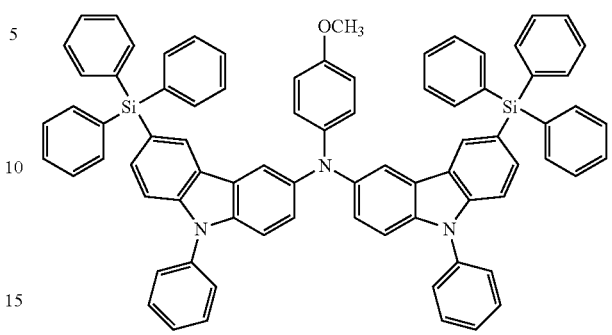

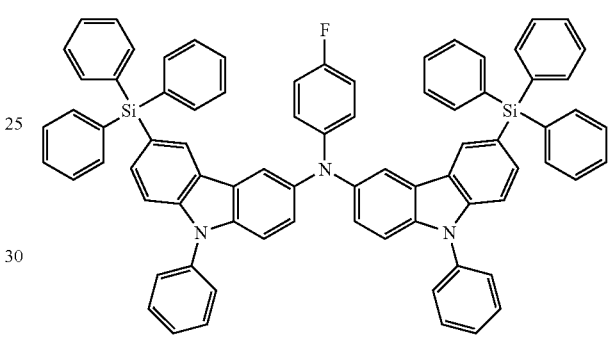

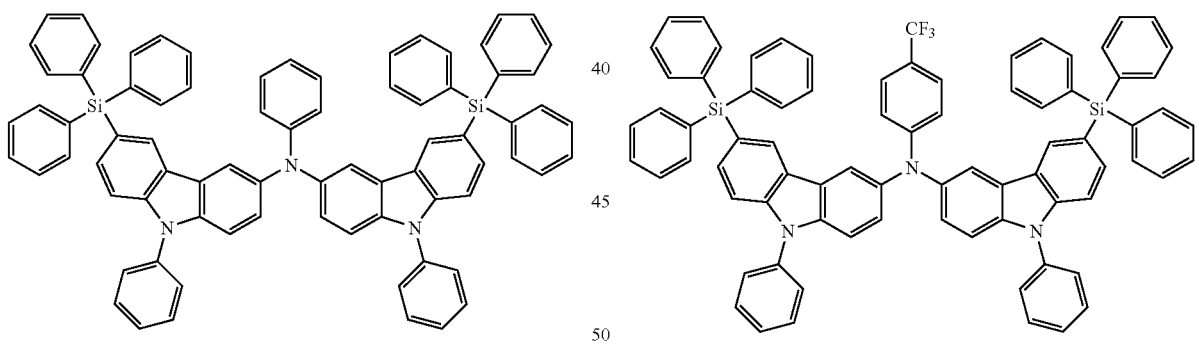

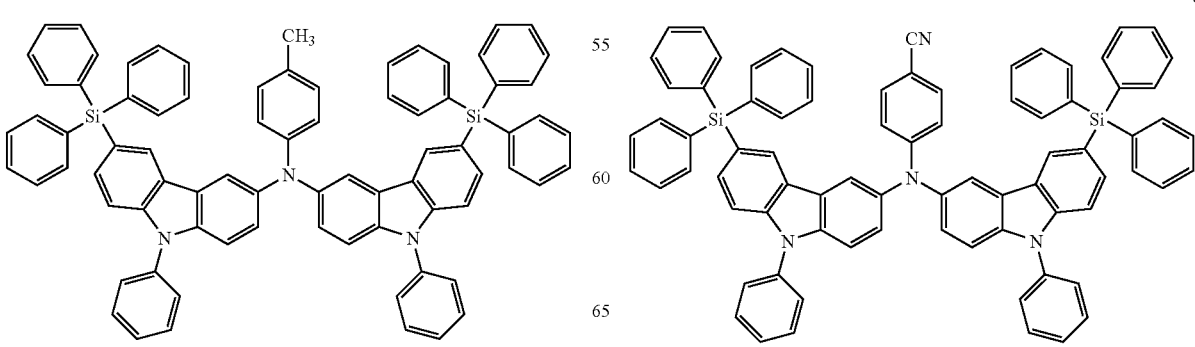

-continued
7
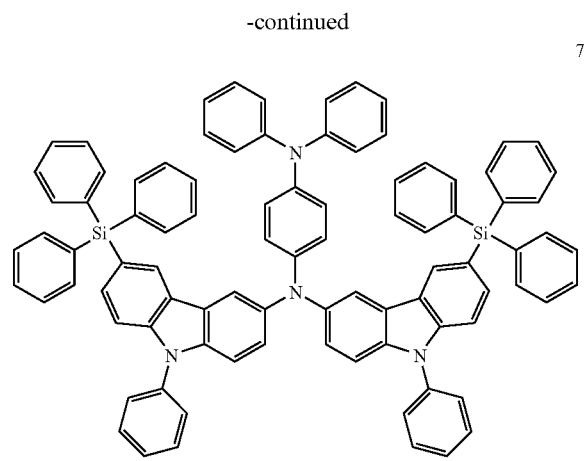
8
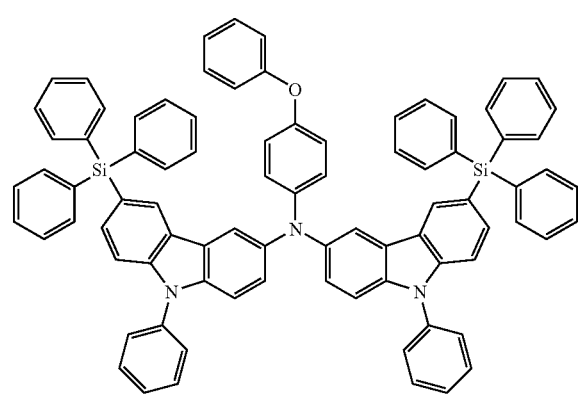
9
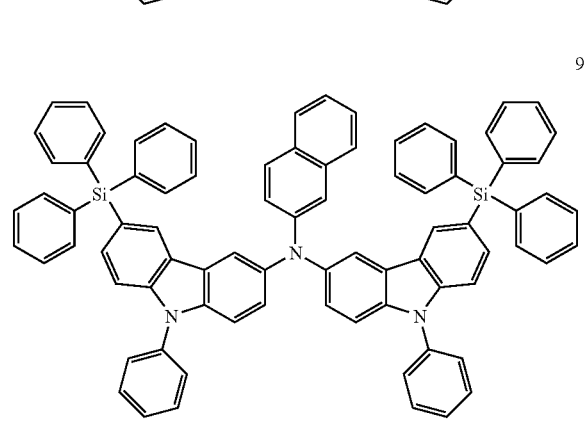
10
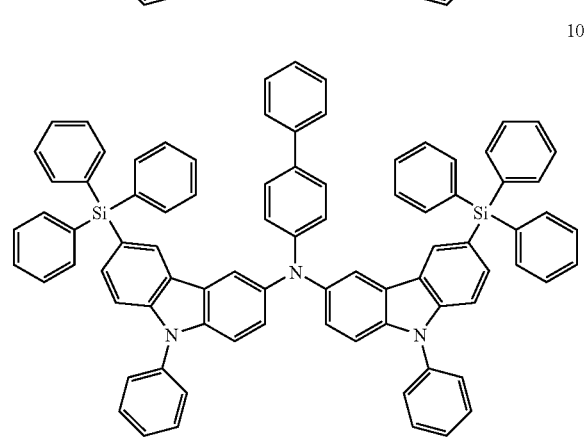
-continued
11
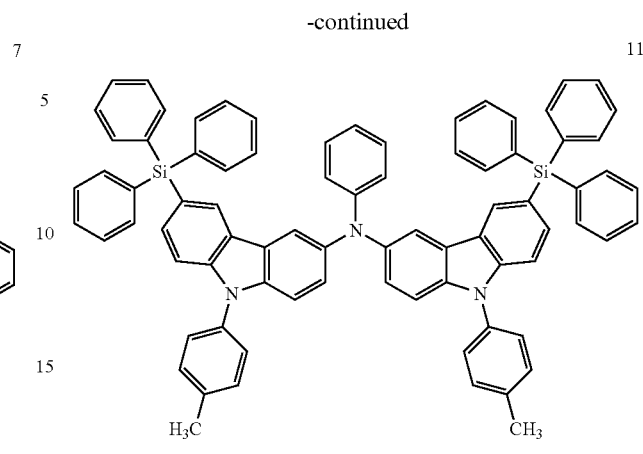
12
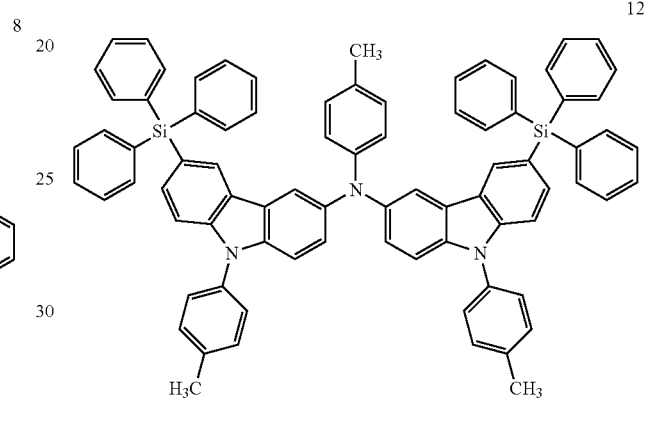
13
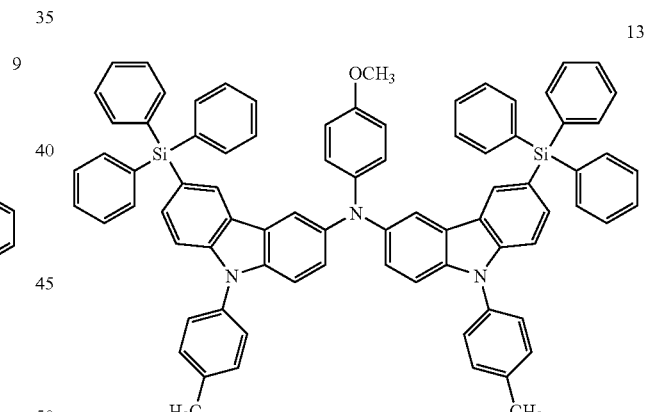
14
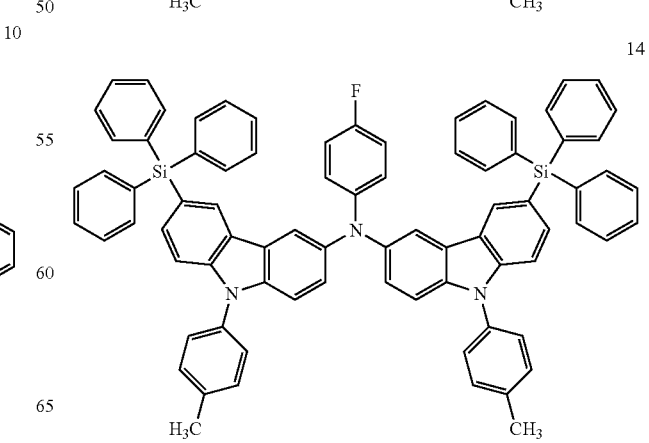

15
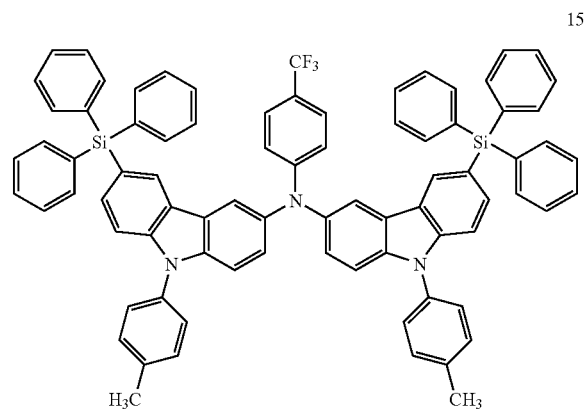
16
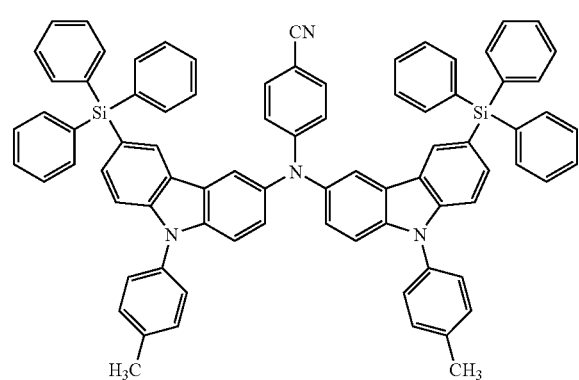
17
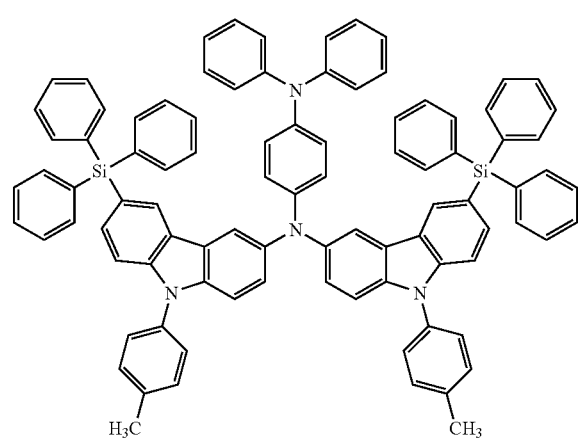
18
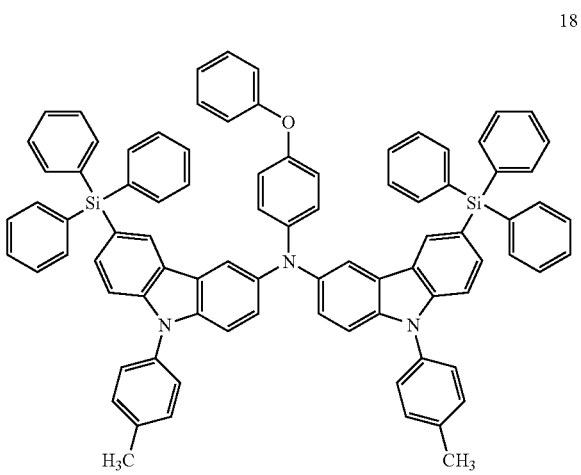
19
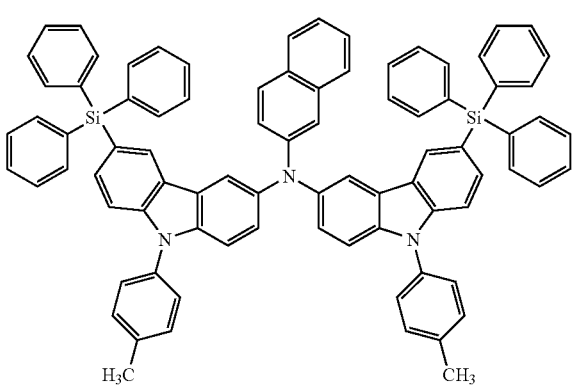
20
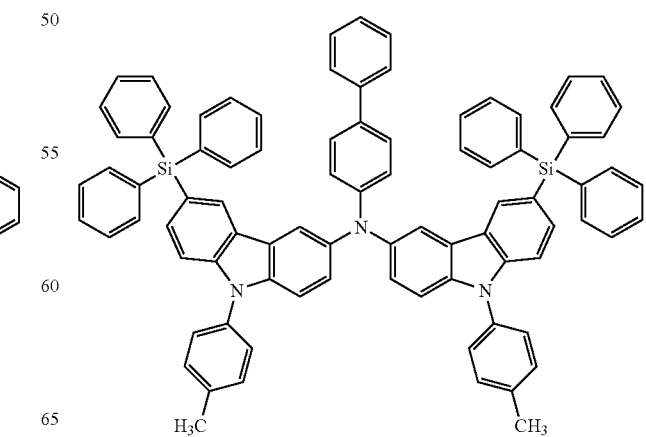

21
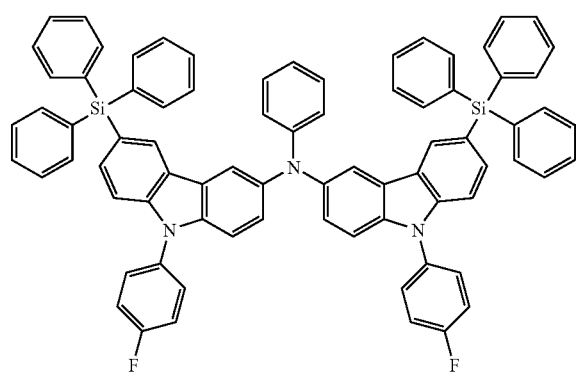
22
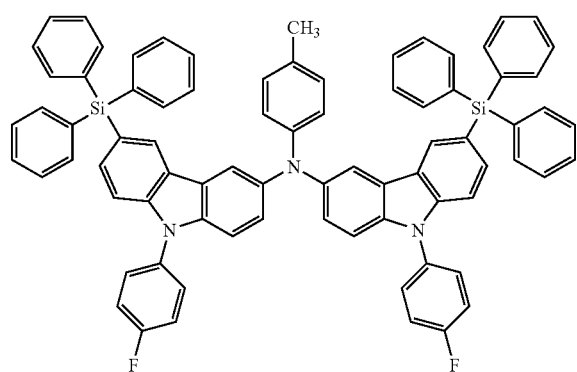
23
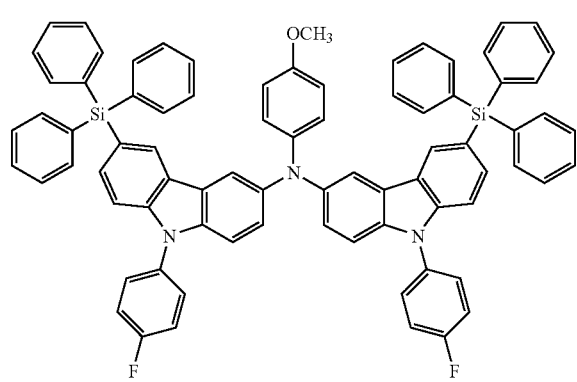
24
25
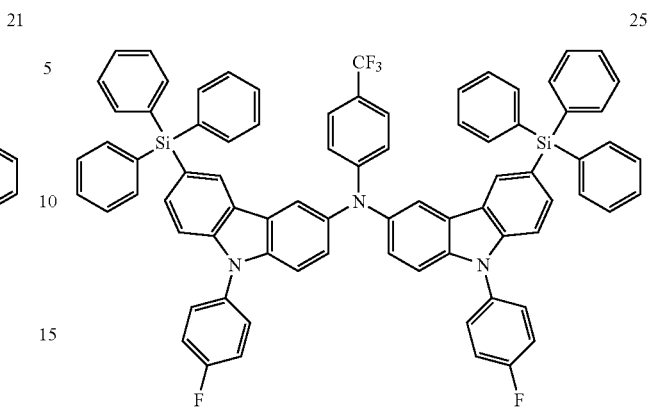
26
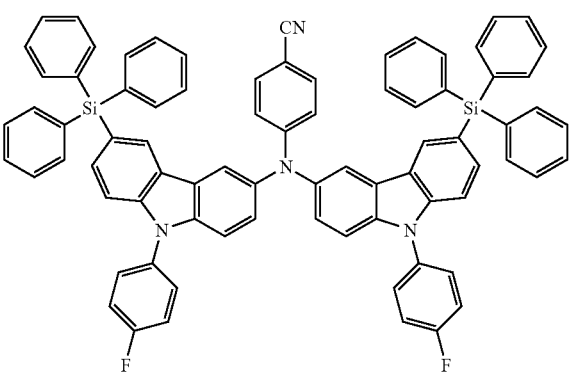
27
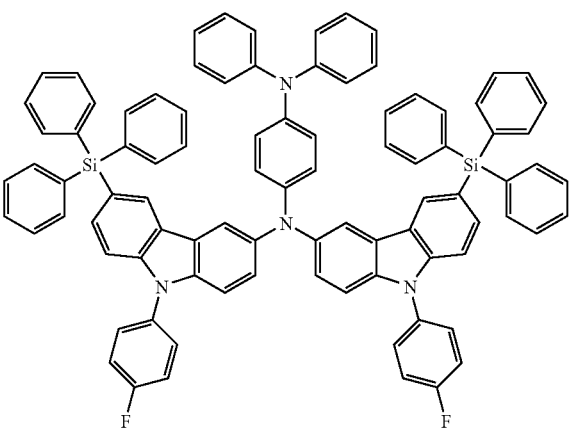

-continued
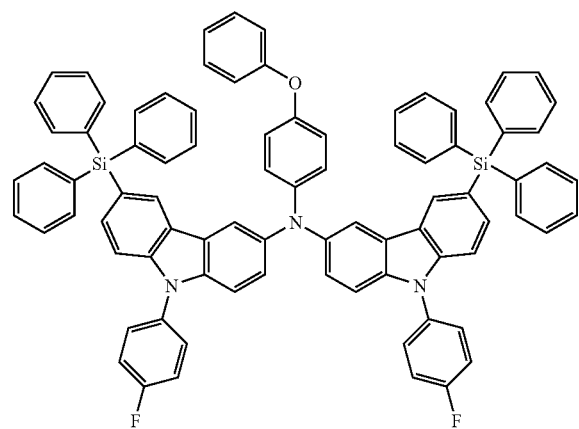
28
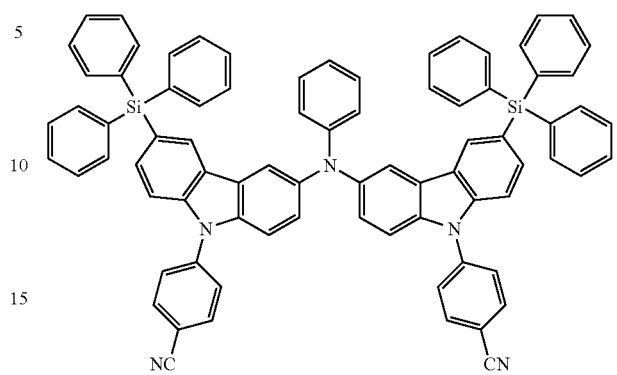
31
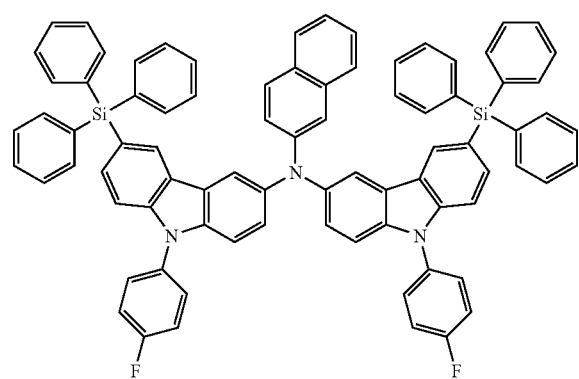
29
32
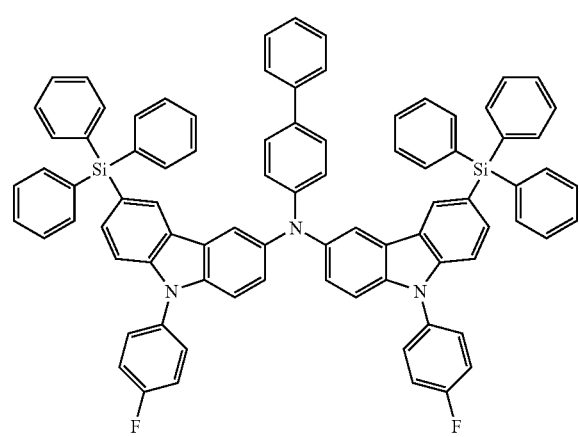
30
33
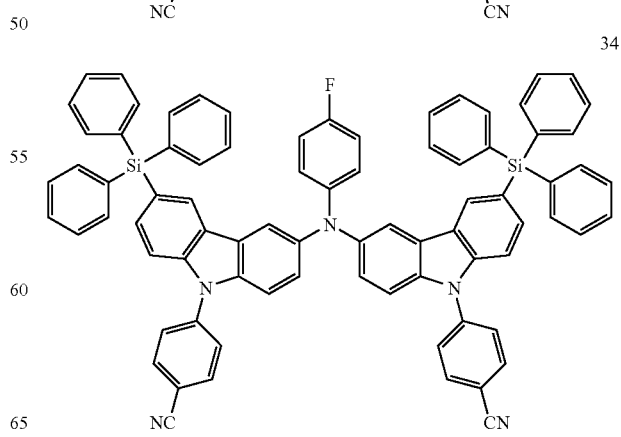
34

-continued
35
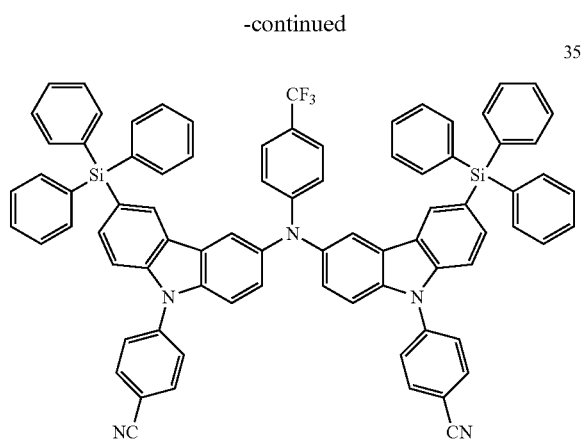
36
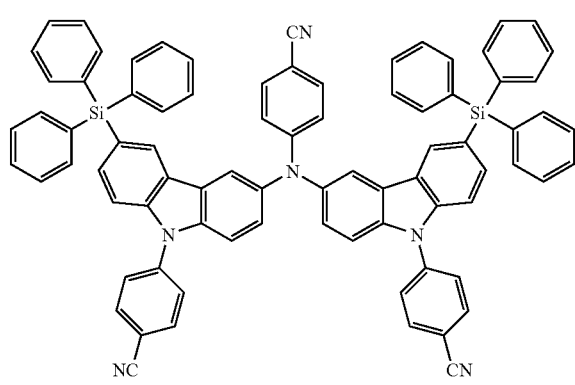
37
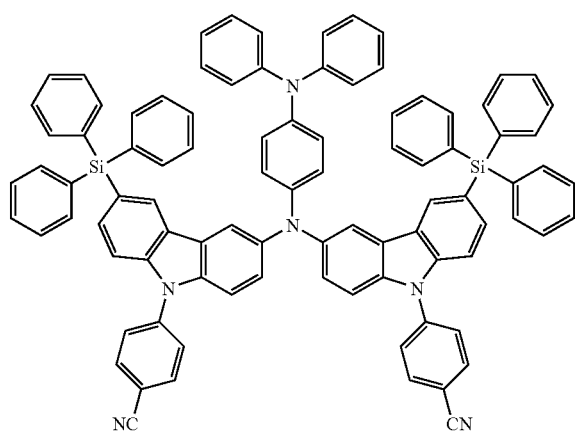
-continued
38
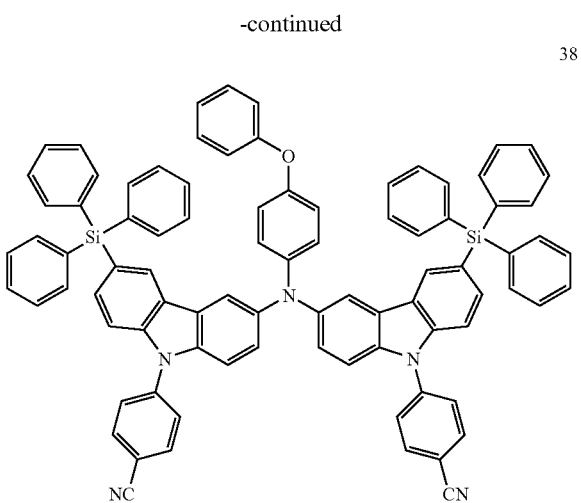
39
40

-continued
41
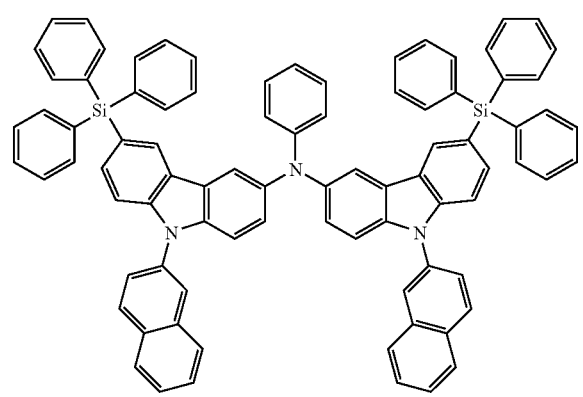
42
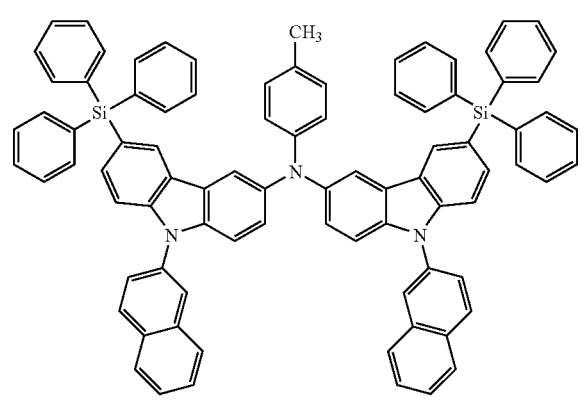
43
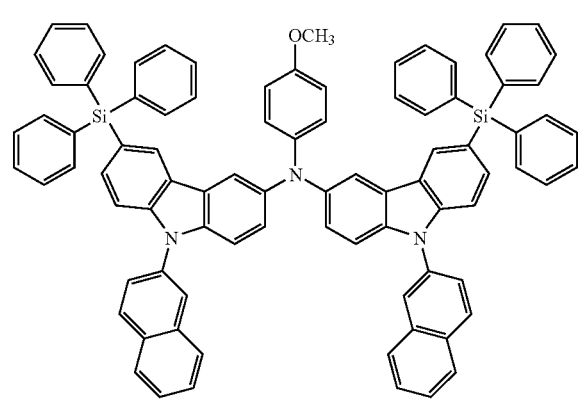
44
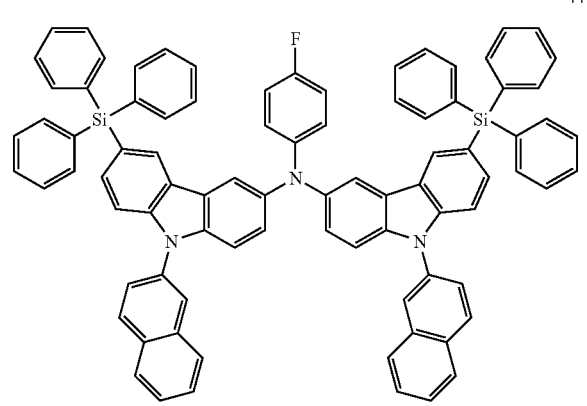
45
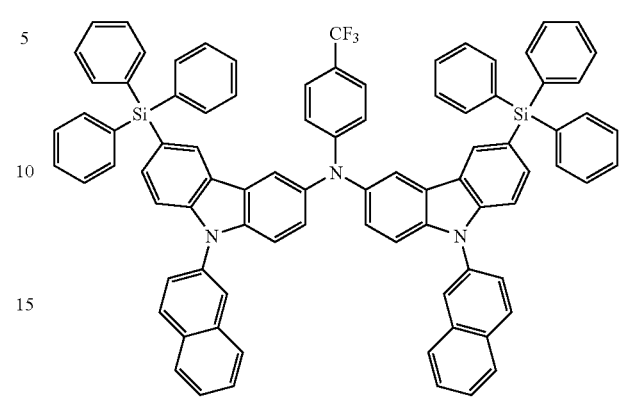
46
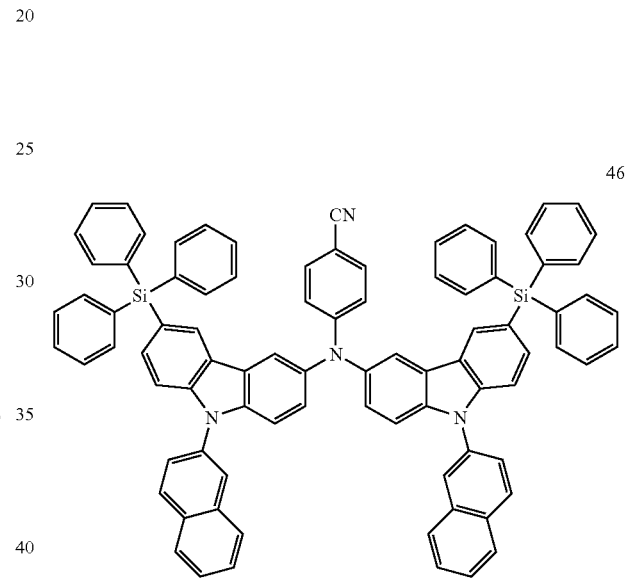
47
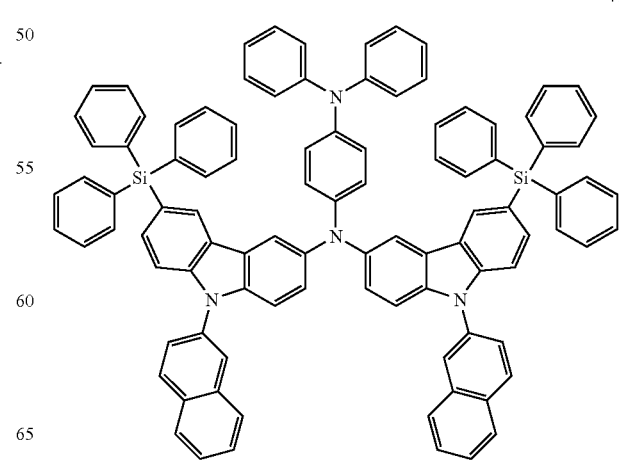

48
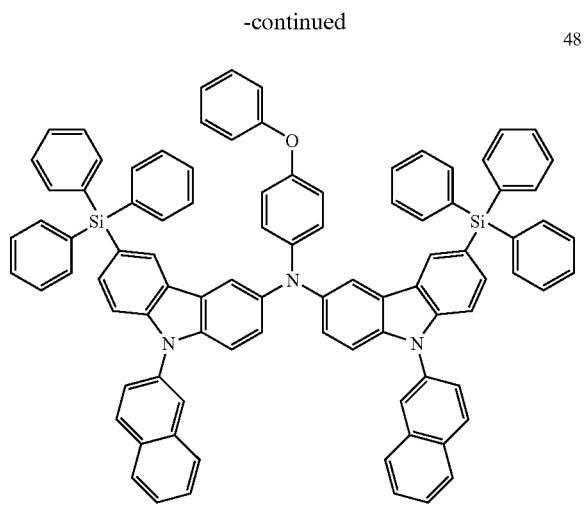
49
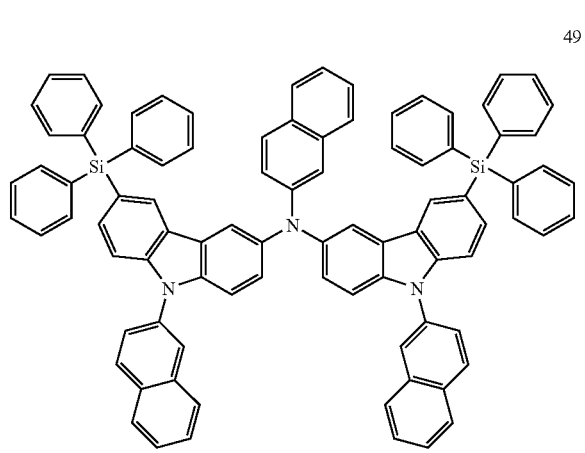
50
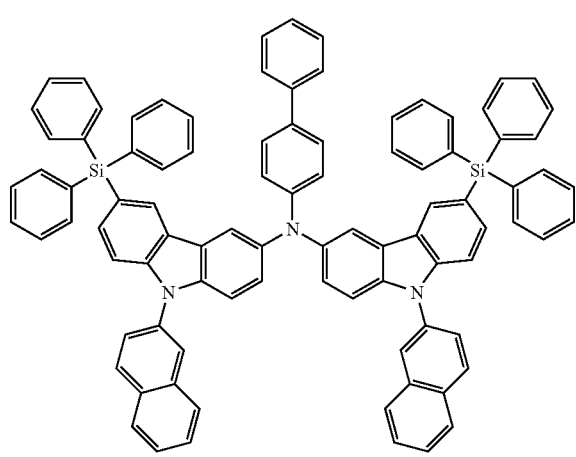
51
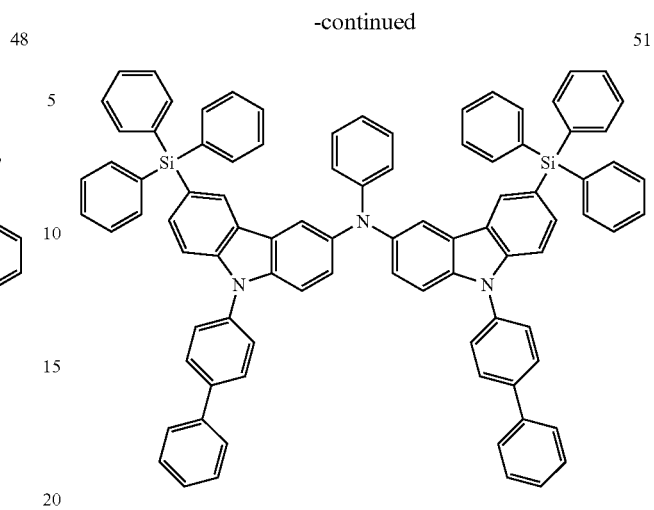
52
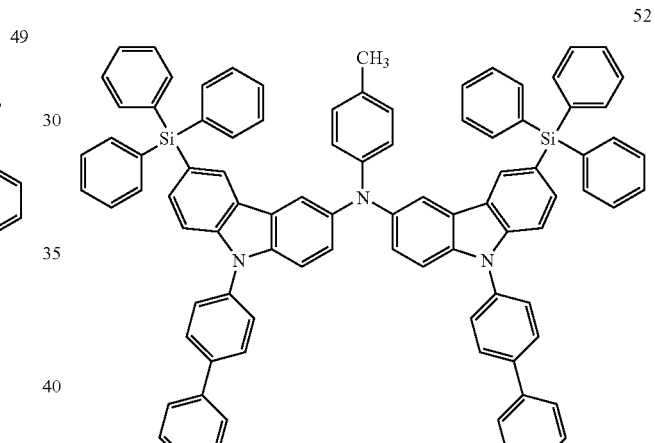
53
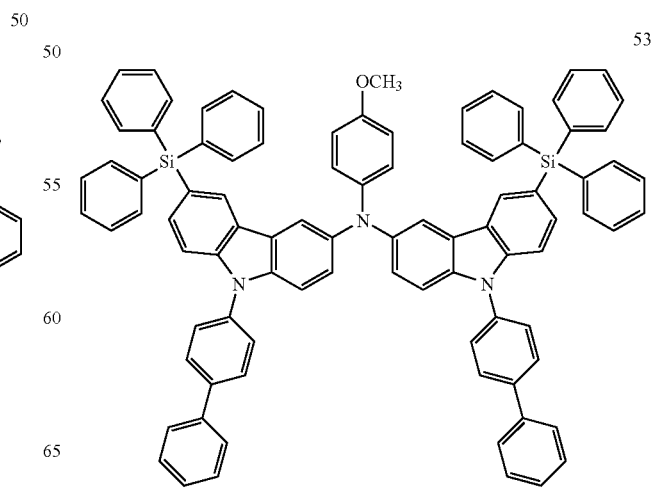

-continued
54
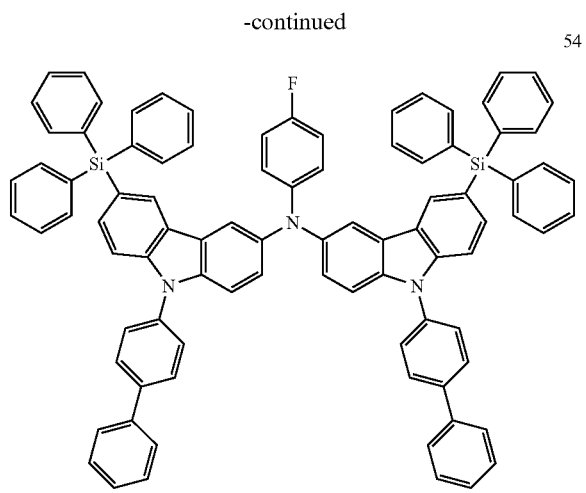
55
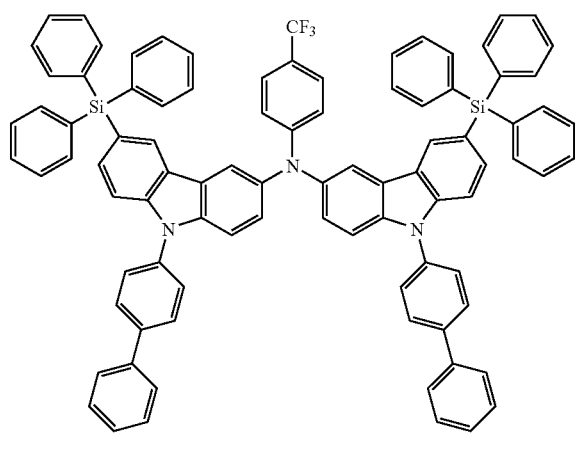
56
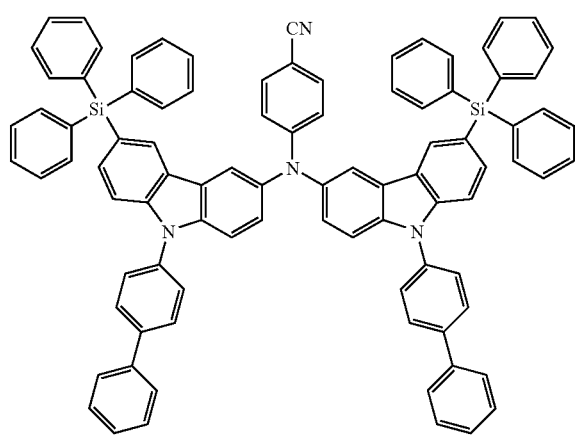
-continued
57
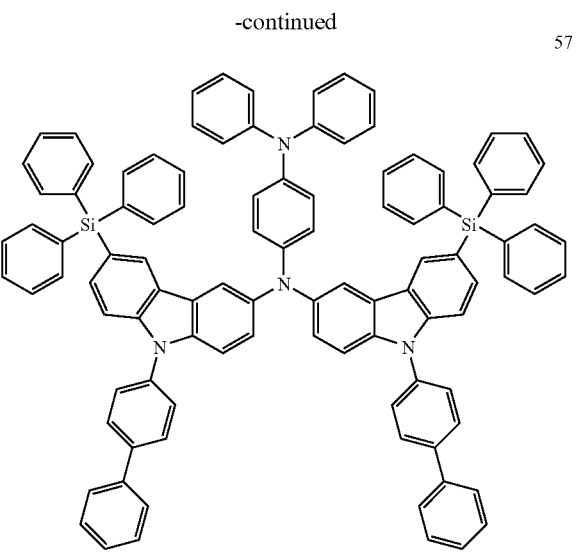
58
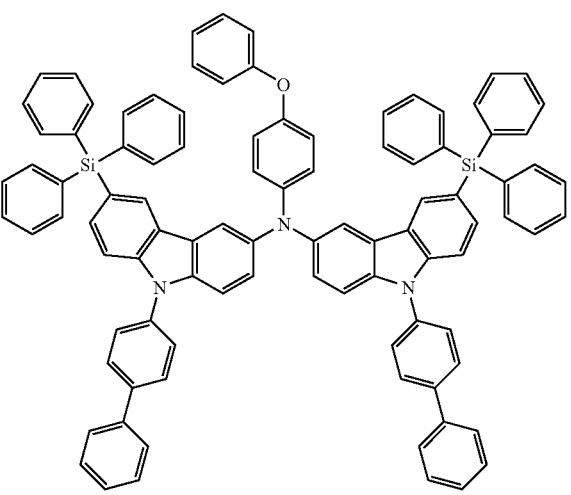
59
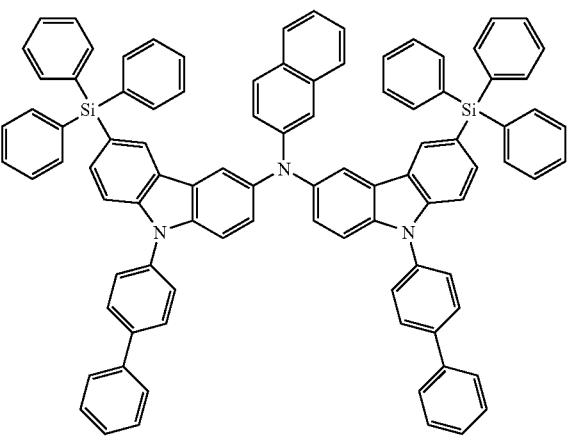

-continued

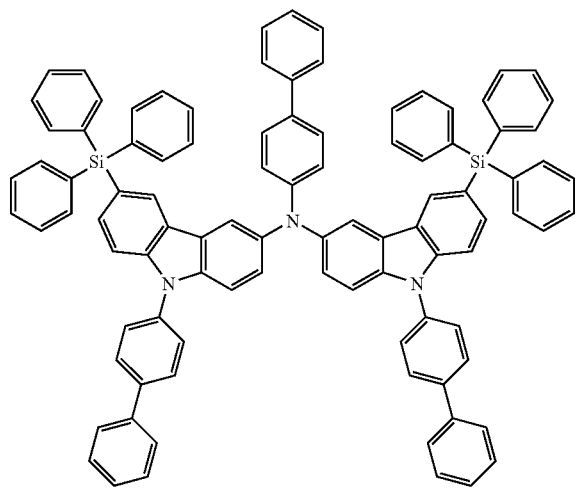

Aspects of the present invention also provide an organic light-emitting device. Non-limiting examples of organic light-emitting devices are shown in FIGS. 1-8. For example, FIG. 1 show an organic light-emitting device including: a first electrode, a second electrode, and one or more organic layers interposed between the first electrode and the second electrode, wherein at least one of the one or more organic layers includes the silanylamine-based compound of Formula 1. The organic layer including the silanylamine-based compound of Formula 1 may be a hole injection layer, a hole transport layer, or a single layer having hole injection capability and hole transport capability. The organic layer including the silanylamine-based compound of Formula 1 may also be an emitting layer. The emitting layer may include a phosphorescent or fluorescent material. Meanwhile, the first electrode may be an anode and the second electrode may be a cathode. Of course, the first electrode and the second electrode may also be a cathode and an anode, respectively.

The above-described organic light-emitting device may further include at least one of a hole injection layer, a hole transport layer, an electron blocking layer, an emitting layer, a hole blocking layer, an electron transport layer, and an electron injection layer, when needed. For example, the organic light-emitting device according to aspects of the present invention may have one of the following structures:

first electrode/hole injection layer/emitting layer/second electrode (FIG. 2);

first electrode/hole injection layer/hole transport layer/emitting layer/electron transport layer/second electrode (FIG. 3); or first electrode/hole injection layer/hole transport layer/emitting layer/electron transport layer/electron injection layer/second electrode (FIG. 4).

The organic light-emitting device may also have a single layer having hole injection capability and hole transport capability and may have one of the following structures:

first electrode/single layer having hole injection capability and hole transport capability/emitting layer/electron transport layer/second electrode (FIG. 5), or first electrode/single layer having hole injection capability and hole transport capability/emitting layer/electron transport layer/electron injection layer/second electrode (FIG. 6).

Hereinafter, a method of manufacturing an organic light-emitting device according to an embodiment of the present invention will be described with reference to FIG. 8. Referring to FIG. 8, an organic light-emitting device may include a substrate, a first electrode (anode), a hole injection layer (HIL), a hole transport layer (HTL), an emitting layer (EML), an electron transport layer (ETL), an electron injection layer (EIL), and a second electrode (cathode).

First, a first electrode is formed on a substrate by deposition or sputtering using a first electrode material with a high work function. The first electrode may be an anode or a cathode. Here, the substrate may be a substrate commonly used in organic light-emitting devices. As a non-limiting example, the substrate may be a glass or transparent plastic substrate which is excellent in mechanical strength, thermal stability, transparency, surface smoothness, handling property, and water repellency. The first electrode material may be a material with good conductivity, e.g., indium tin oxide (ITO), indium zinc oxide (IZO), tin oxide ($SnO_2$), zinc oxide (ZnO), Al, Ag, or Mg, and may form a transparent electrode or a reflective electrode.

Next, a hole injection layer (HIL) may be formed on the first electrode using any one of various methods, such as vacuum deposition, spin-coating, casting, or Langmuir-Blodgett (LB) method.

When a vacuum deposition process is used to form the hole injection layer, the deposition conditions may vary according to the type of a hole injection layer material, the structure and thermal characteristics of the hole injection layer, etc. As a non-limiting example, the hole injection layer may be deposited to a thickness of 10 Å to 5 μm at a deposition rate of 0.01 to 100 Å/sec, at a temperature of 100 to 500° C., and in a vacuum level of $10^{-8}$ to $10^{-3}$ torr.

When a spin-coating process is used to form the hole injection layer, the coating conditions may vary according to the type of a hole injection layer material, the structure and thermal characteristics of the hole injection layer, etc. As a non-limiting example, the spin-coating may be performed at a coating speed of about 2,000 to 5,000 rpm, and, after the spin-coating, a thermal treatment may be performed at a temperature of about 80 to 200° C. for the purpose of solvent removal.

The hole injection layer material may be a silanylamine-based compound of Formula 1 as described above. In addition, the hole injection layer material may be a known hole injection layer material, e.g., a phthalocyanine compound (e.g., copper phthalocyanine) disclosed in U.S. Pat. No. 4,356,429, a Starburst-type amine derivative (e.g., TCTA, m-MTDATA, or m-MTDAPB) disclosed in *Advanced Material,* 6, p. 677 (1994), or a soluble conductive polymer, e.g., polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly(4-styrenesulfonate) (PANI/PSS).

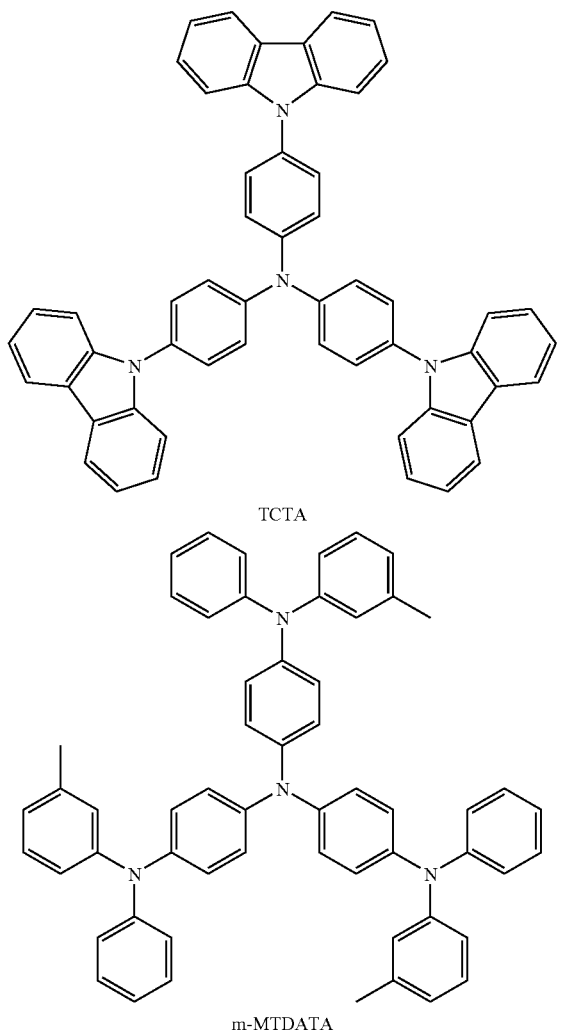

TCTA m-MTDATA

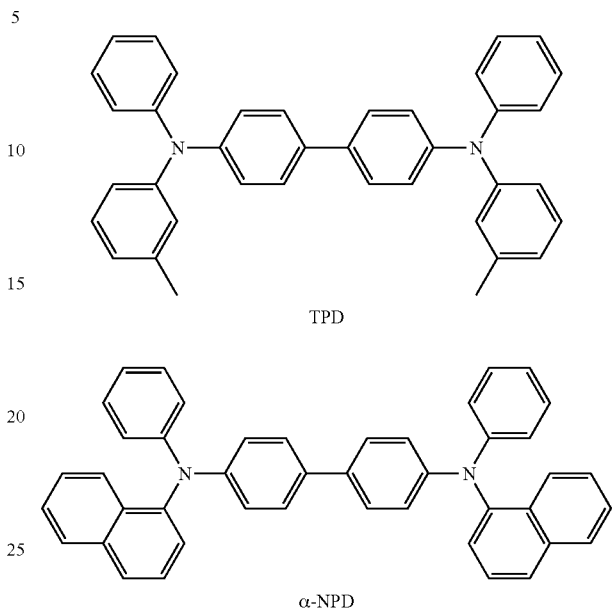

TPD

α-NPD

The hole injection layer may be formed to a thickness of about 100 to 10,000 Å. As a non-limiting example, the hole injection layer may be formed to a thickness of about 100 to 1,000 Å. If the thickness of the hole injection layer is less than 100 Å, hole injection characteristics may be lowered. On the other hand, if the thickness of the hole injection layer exceeds 10,000 Å, a driving voltage may be increased.

Next, a hole transport layer (HTL) may be formed on the hole injection layer using any one of various methods, such as vacuum deposition, spin-coating, casting, or LB method. When vacuum deposition or spin-coating are used to form the hole transport layer, the deposition or coating conditions may vary according to the type of compound used, but are generally about the same as those used for the formation of the hole injection layer.

The hole transport layer material may be a silanylamine-based compound of Formula 1 as described above. In addition, the hole transport layer material can be a known hole transport layer material, e.g., a carbazole derivative such as N-phenylcarbazole or polyvinylcarbazole; an amine derivative having an aromatic fused ring such as 4,4'-bis[N-(1-naphthyl)-N-phenylamino]biphenyl (NPB), N,N'-bis(3-methylphenyl)-N,N'-diphenyl-[1,1-biphenyl]-4,4'-diamine (TPD), or N,N'-di(naphthalene-1-yl)-N,N'-diphenylbenzidine (α-NPD); etc.

The hole transport layer may be formed to a thickness of about 50 to 1,000 Å. As a non-limiting example, the hole transport layer may be formed to a thickness of about 100 to 600 Å. If the thickness of the hole transport layer is less than 50 Å, hole transport characteristics may be lowered. On the other hand, if the thickness of the hole transport layer exceeds 1,000 Å, a driving voltage may be increased.

Next, an emitting layer (EML) may be formed on the hole transport layer using vacuum deposition, spin-coating, casting, or LB method. In the case of forming the emitting layer using When vacuum deposition or spin-coating are used to form the emitting layer, the deposition or coating conditions may vary according to the type of compound used, but are generally about the same as those used for the formation of the hole injection layer.

The emitting layer may include a silanylamine-based compound of Formula 1 as described above. In addition, the emitting layer may be formed of various known emitting materials or known host/dopants. With respect to a dopant, known fluorescent or phosphorescent dopants can be used.

$Alq_3$, 4,4'-N,N'-dicarbazole-biphenyl (CBP), poly(n-vinylcarbazole) (PVK), distyrylarylene (DSA), IDE215 (Idemitsu), etc. may be used as a host, but the present invention is not limited thereto.

The dopant may be a fluorescent dopant such as IDE102, IDE105, and IDE118, which are commercially available from Idemitsu, or a phosphorescent dopant such as Ir(ppy)$_3$ (ppy: phenylpyridine)(green), (4,6-F2 ppy)$_2$Irpic (reference: Chihaya Adachi etc. *Appl. Phys. Lett.*, 79, 2082-2084, 2001), TEB002 (Covion Co.), platinum(II) octaethylporphyrin (PtOEP), a compound represented by Formula 3 below (see Korean Patent Laid-Open Publication No. 2005-0078472), Firpric, or a red phosphorescent dopant (RD1, UDC), but the present invention is not limited thereto.

<Formula 3>

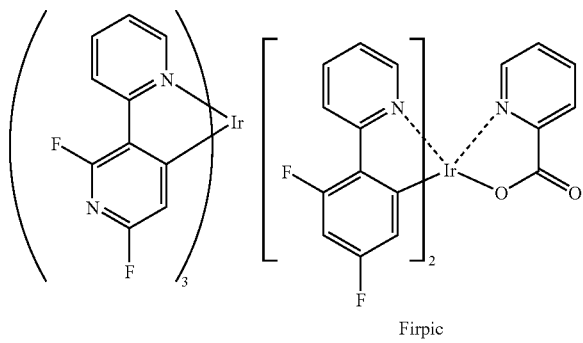

Firpic

The content of a dopant may be 0.1 to 20 parts by weight or 0.5 to 12 parts by weight, based on 100 parts by weight (i.e., the total weight of a host and the dopant) of an emitting layer material. If the content of the dopant is less than 0.1 parts by weight, a dopant addition effect may be insufficient. On the other hand, if it exceeds 20 parts by weight, the concentration quenching of both phosphorescence and fluorescence may occur.

The emitting layer may be formed to a thickness of about 100 to 1,000 Å, preferably 200 to 600 Å. If the thickness of the emitting layer is less than 100 Å, emission characteristics may be lowered. On the other hand, if the thickness of the emitting layer exceeds 1,000 Å, a driving voltage may be increased.

If the emitting layer includes a phosphorescent dopant, a hole blocking layer (HBL) (FIG. 7) may be formed on the emitting layer in order to prevent the diffusion of triplet excitons or holes into an electron transport layer. The hole blocking layer material is not particularly limited and may be optionally selected from known hole blocking layer materials. For example, an oxadiazole derivative, a triazole derivative, a phenanthroline derivative, a hole blocking material disclosed in JP 11-329734(A1), Balq, BCP, etc. may be used.

The hole blocking layer may be formed to a thickness of about 50 to 1,000 Å, or 100 to 300 Å. If the thickness of the hole blocking layer is less than 50 Å, hole blocking characteristics may be lowered. On the other hand, if the thickness of the hole blocking layer exceeds 1,000 Å, a driving voltage may be increased.

Next, an electron transport layer (ETL) may be formed using any one of various methods, such as vacuum deposition, spin-coating, or casting. When vacuum deposition or spin-coating are used to form the electron transport layer, the deposition or coating conditions may vary according to the type of compound used, but are generally about the same as those used for the formation of the hole injection layer.

An electron transport layer material is not particularly limited and may be optionally selected from known electron transport layer materials. For example, a known material such as a quinoline derivative, in particular, tris(8-quinolinolate) aluminum ($Alq_3$), or TAZ (a triazole derivative) may be used.

The electron transport layer may be formed to a thickness of about 100 to 1,000 Å, or 100 to 500 Å. If the thickness of the electron transport layer is less than 100 Å, electron transport characteristics may be lowered. On the other hand, if the thickness of the electron transport layer exceeds 1,000 Å, a driving voltage may be increased.

An electron injection layer (EIL) may be formed on the electron transport layer in order to facilitate the injection of electrons from a cathode. The electron injection layer material may be optionally selected from known materials such as LiF, NaCl, CsF, $Li_2O$, or BaO. The deposition or coating conditions of the electron injection layer may vary according to the type of compound used, but are generally about the same as those used for the formation of the hole injection layer.

The electron injection layer may be formed to a thickness of about 1 to 100 Å, or 5 to 90 Å. If the thickness of the electron injection layer is less than 1 Å, electron injection characteristics may be lowered. On the other hand, if the thickness of the electron injection layer exceeds 100 Å, a driving voltage may be increased.

Finally, a second electrode may be formed on the electron injection layer using vacuum deposition or sputtering. The second electrode may be used as a cathode or an anode. The material for forming the second electrode may be a metal or alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), etc. The second electrode may also be a transmissive cathode formed of ITO or IZO to provide a front-emission type device.

Hereinafter, exemplary synthesis examples of compounds 1, 4, 11, 21, and 22 according to aspects of the present invention and working examples will be described. The following examples are for illustrative purposes only and are not intended to limit the scope of the invention.

It is to be understood that the organic light-emitting device is not limited to the above-described structures and that other structures may be used.

EXAMPLES

Synthesis Example 1

Synthesis of Compound 1

A compound 1 was synthesized according to Reaction Scheme 1 below.

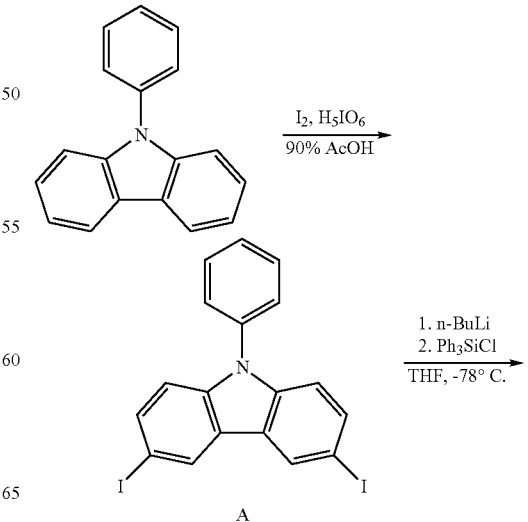

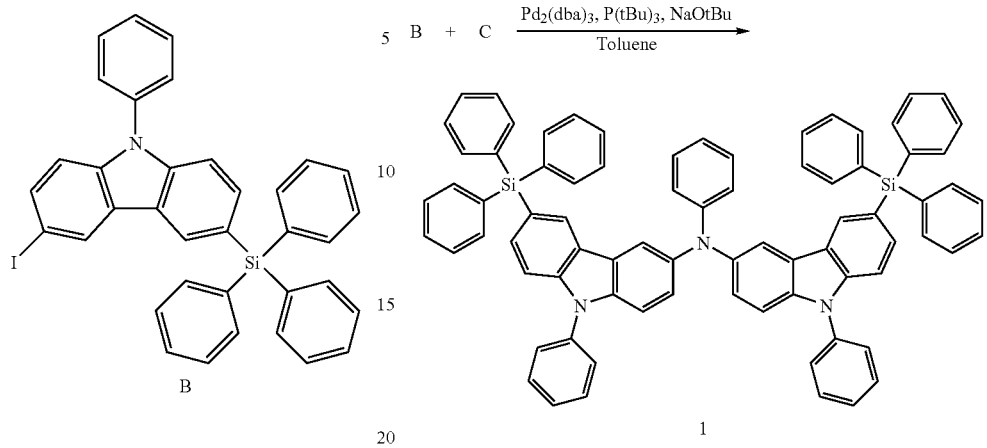

Synthesis of Intermediate A

Carbazole (2.433 g, 10 mmol) was added to an 80% acetic acid (100 ml), and iodine (I$_2$) (2.714 g, 10.7 mmol) and ortho-periodinic acid (H$_5$IO$_6$) (0.666 g, 2.92 mmol) in a solid phase were added thereto. The reaction mixture was stirred at 8° C. under a nitrogen atmosphere for three hours. After the reaction was terminated, the reaction solution was extracted three times with ethylacetate (50 ml). The collected organic layer was dried over magnesium sulfate to evaporate the solvent. The resultant residue was purified by silica gel column chromatography to give an intermediate A as a white solid (4.21 g, yield: 85%). $^1$H NMR (CDCl$_3$, 400 MHz) δ (ppm) 8.28 (m, 2H), 7.72 (d, 2H), 7.56-7.32 (m, 7H); $^{13}$C NMR (CDCl$_3$, 100 MHz) δ (ppm) 139.1, 135.8, 130.6, 129.8, 127.4, 127.1, 123.0, 121.1, 116.3, 84.9.

Synthesis of Intermediate B

The intermediate A (4.95 g, 10 mmol) was dissolved in THF (30 ml), and n-butyllithium (4 ml, 2.5M in hexane) was added thereto at −78° C. One hour after the addition, a solution of chlorotriphenylsilane (2.95 g, 10 mmol) in THF (5 ml) was gradually added thereto at −78° C. The reaction mixture was stirred at room temperature for five hours, and water was added thereto. The reaction solution was extracted three times with diethylether (30 ml). The obtained diethylether layer was dried over MgSO$_4$, and then dried under a reduced pressure to obtain a crude product. The crude product was purified by silica gel column chromatography to give an intermediate B as a white solid (3.58 g, yield: 57%). $^1$H NMR (CDCl$_3$, 400 MHz) δ (ppm) 8.65-8.58 (m, 2H), 8.30 (s, 1H), 8.12 (dd, 1H), 7.75-7.15 (m, 22H) $^{13}$C NMR (CDCl$_3$, 100 MHz) δ (ppm) 139.8, 137.7, 135.7, 135.1, 133.0, 132.8, 131.7, 130.6, 129.8, 129.6, 127.9, 127.4, 127.1, 123.4, 121.7, 121.6, 119.6, 113.4, 113.1, 110.5.

Synthesis of intermediate C

The intermediate B (0.537 g, 0.856 mmol) and aniline (0.112 g, 1.2 mmol) were dissolved in toluene (5 ml), and t-BuONa (0.144 g, 1.5 mmol), Pd(dba)$_2$ (0.018 g, 0.02 mmol), and (t-Bu)$_3$P (0.004~0.006 g, 0.02~0.03 mmol) were added thereto. The reaction mixture was stirred at 80° C. for five hours. The reaction solution was extracted three times with ethylether (20 ml). The collected organic layer was dried over magnesium sulfate to evaporate a solvent. The resultant residue was purified by silica gel column chromatography to give an intermediate C (0.345 g, yield: 68%). $^1$H NMR (CDCl$_3$, 400 MHz) δ (ppm) 8.62-8.53 (m, 2H), 8.12 (dd, 1H), 7.68-6.71 (m, 28H), 6.54 (bs, 1H); $^{13}$C NMR (CDCl$_3$, 100 MHz) δ (ppm) 144.6, 140.5, 135.7, 135.1, 133.6, 133.2, 132.5, 131.7, 129.8, 129.3, 129.6, 129.3, 127.9, 127.4, 127.1, 124.3, 122.3, 120.4, 119.0, 116.7, 115.9, 113.8, 111.1, 109.3, 102.4.

Synthesis of Compound 1

The intermediate B (6.28 g, 10 mmol), the intermediate C (7.11 g, 12 mmol), t-BuONa (2.9 mg, 30 mmol), Pd$_2$(dba)$_3$ (183 mg, 0.2 mmol), and P(t-Bu)$_3$ (40 mg, 0.2 mmol) were dissolved in toluene (40 ml), and the reaction mixture was stirred at 90° C. for three hours. After the reaction was terminated, the reaction solution was cooled to room temperature and extracted three times with distilled water and diethylether (40 ml). The collected organic layer was dried over magnesium sulfate to evaporate the solvent. The resultant residue was purified by silica gel column chromatography to give the compound 1 (8.96 g, yield: 82%). $^1$H NMR (CDCl$_3$, 400 MHz) δ (ppm) 8.81-8.75 (m, 3H), 8.44 (s, 1H), 8.12 (dd, 2H), 7.79-6.60 (m, 51H) $^{13}$C NMR (CDCl$_3$, 100 MHz) δ (ppm) 147.6, 145.6, 141.0, 138.5, 136.1, 135.7, 135.1, 134.9, 133.7, 132.6, 132.5, 131.7, 131.3, 129.8, 129.6, 129.3, 127.9, 127.4, 127.1, 125.8, 122.9, 122.1, 121.7, 117.9, 116.3, 115.7, 114.7, 112.8, 110.6, 109.7, 107.5, 103.3.

Synthesis Example 2

Synthesis of Compound 4

A compound 4 was synthesized according to Reaction Scheme 2 below.

<Reaction Scheme 2>

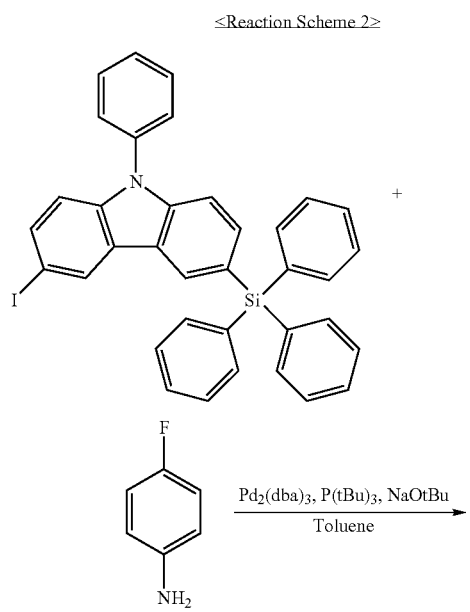

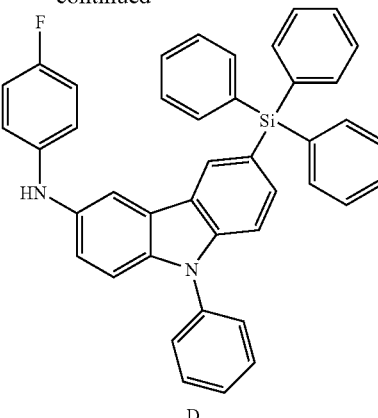

D

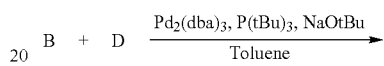

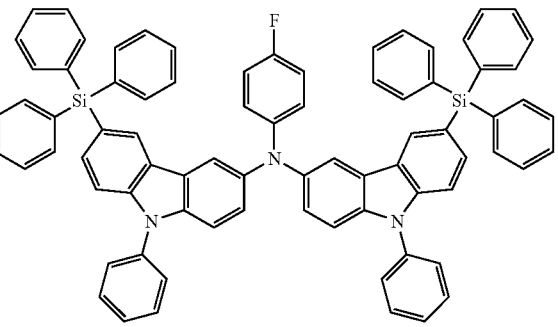

4

Synthesis of intermediate D

The intermediate B (0.537 g, 0.856 mmol) and 4-fluoroaniline (0.133 g, 1.2 mmol) were dissolved in toluene (5 ml), and t-BuONa (0.144 g, 1.5 mmol), Pd(dba)$_2$ (0.018 g, 0.02 mmol), and (t-Bu)$_3$P (0.004~0.006 g, 0.02~0.03 mmol) were added thereto. The reaction mixture was stirred at 80° C. for five hours. The reaction solution was extracted three times with ethylether (20 ml). The collected organic layer was dried over magnesium sulfate to evaporate to the solvent. The resultant residue was purified by silica gel column chromatography to give an intermediate D (0.371 g, yield: 71%). $^1$H NMR (CDCl$_3$, 400 MHz) δ (ppm) 8.61 (d, 2H), 8.53 (s, 1H), 8.12 (dd, 1H), 7.95-6.94 (m, 26H), 6.94 (bs, 1H); $^{13}$C NMR (CDCl$_3$, 100 MHz) δ (ppm) 159.0, 156.4, 140.7, 140.5, 135.7, 135.1, 133.6, 133.4, 133.0, 131.7, 129.8, 129.6, 127.9, 127.4, 127.1, 123.3, 122.3, 120.4, 116.2, 115.9, 113.8, 111.6, 111.5, 111.1, 109.3, 99.7.

Synthesis of Compound 4

The intermediate B (6.28 g, 10 mmol), the intermediate D (7.33 g, 12 mmol), t-BuONa (2.9 mg, 30 mmol), Pd$_2$(dba)$_3$ (183 mg, 0.2 mmol), and P(t-Bu)$_3$ (40 mg, 0.2 mmol) were dissolved in toluene (40 ml), and the reaction mixture was stirred at 90° C. for three hours. After the reaction was terminated, the reaction solution was cooled to room temperature and extracted three times with distilled water and diethylether (40 ml). The collected organic layer was dried over magnesium sulfate to evaporate the solvent. The resultant residue was purified by silica gel column chromatography to give the compound 4 (8.66 g, yield: 78%). $^1$H NMR (CDCl$_3$, 400 MHz) δ (ppm) 8.76 (d, 1H), 8.44 (s, 1H), 8.12 (dd, 1H), 7.64-6.74 (m, 53H); $^{13}$C NMR (CDCl$_3$, 100 MHz) δ (ppm) 158.7 (d), 145.6 (d), 138.9 (d), 135.7, 135.1, 134.9, 132.6, 132.5, 131.7, 129.8, 129.6, 127.9, 127.4, 127.1, 125.1, 125.0, 121.7, 120.3, 117.9, 116.3, 115.9, 115.6, 112.8, 110.6, 108.1.

Synthesis Example 3

Synthesis of Compound 11

A compound 11 was synthesized according to Reaction Scheme 3 below.

<Reaction Scheme 3>

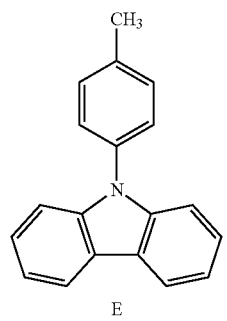

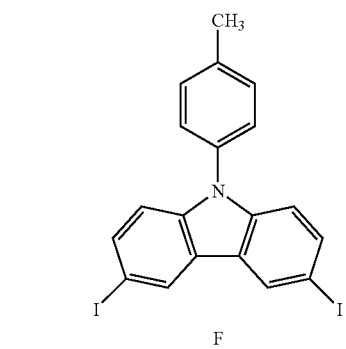

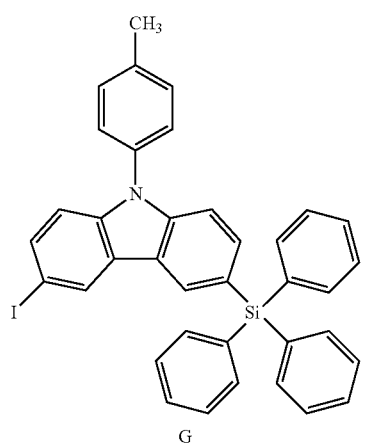

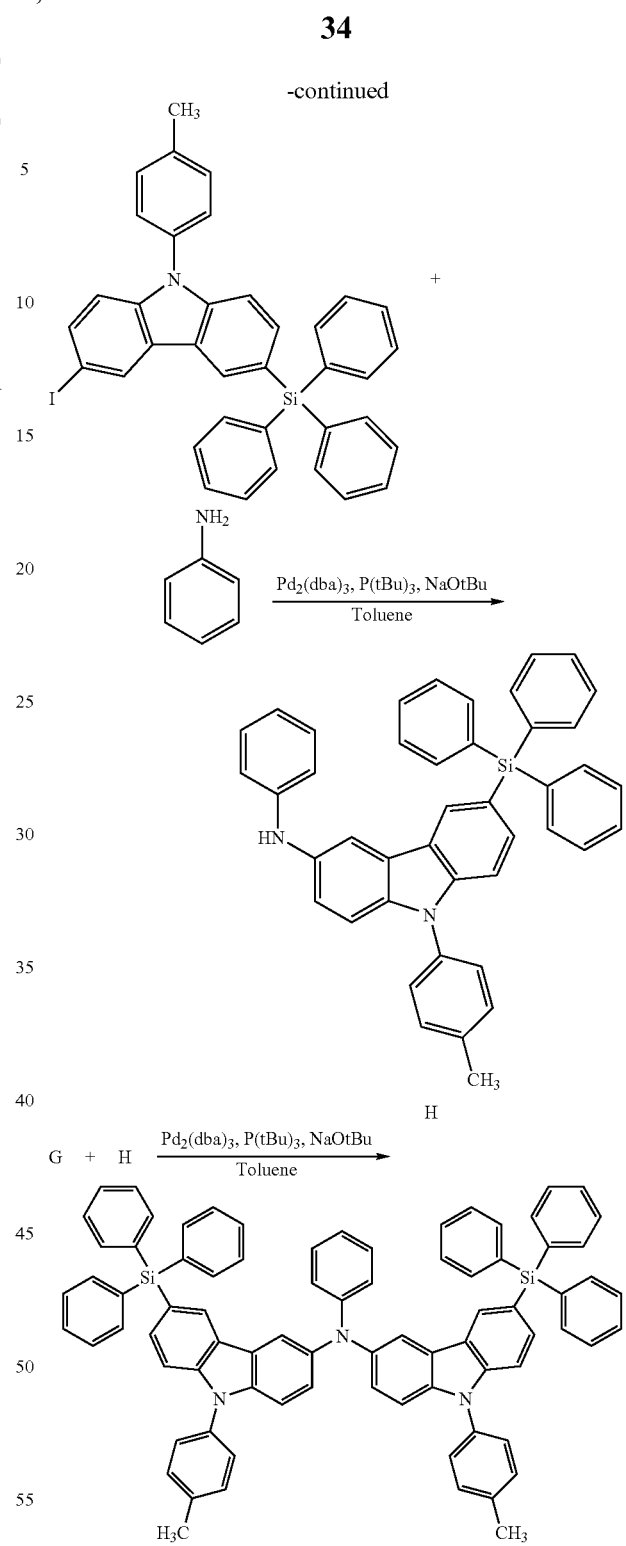

Synthesis of Intermediate E

Carbazole (16.7 g, 100 mmol), 4-iodotoluene (28.3 g, 130 mmol), CuI (1.9 g, 10 mmol), K$_2$CO$_3$ (138 g, 1.0 mol), and 18-crown-6 (530 mg, 2 mmol) were dissolved in 1,3-dimethyl-3,4,5,6-tetrahydro-(1H)-pyrimidinone (DMPU) (500 ml), and the reaction mixture was stirred at 170° C. for eight hours. After the reaction was terminated, the reaction solution was cooled to room temperature, and a solid material was filtered out. A trace amount of an ammonia solution was added to the filtrate, and the resultant solution was extracted three times with diethylether (300 ml). The collected diethylether layer was washed with excess distilled water, dried over MgSO$_4$, filtered, and dried under a reduced pressure to obtain a crude product. The crude product was purified by silica gel column chromatography to give an intermediate E as a white solid (23.4 g, yield: 91%). $^1$H NMR (CDCl$_3$, 400 MHz) δ (ppm) 8.09 (d, 2H), 7.73-7.20 (m, 10H), 2.41 (s, 3H); $^{13}$C NMR (CDCl$_3$, 100 MHz) δ (ppm) 140.4, 138.8, 130.3, 129.7, 126.2, 123.0, 120.7, 120.3, 119.9, 109.6, 20.1.

Synthesis of Intermediate F

The intermediate E (2.57 g, 10 mmol) was added to an 80% acetic acid (100 ml), and iodine (I$_2$) (2.714 g, 10.7 mmol) and ortho-periodinic acid (H$_5$IO$_6$) (0.666 g, 2.92 mmol) in a solid phase were added thereto. The reaction mixture was stirred at 80° C. under a nitrogen atmosphere for three hours. After the reaction was terminated, the reaction solution was extracted three times with ethylether (50 ml). The collected organic layer was dried over magnesium sulfate to evaporate the solvent. The resultant residue was purified by silica gel column chromatography to give an intermediate F as a white solid (4.43 g, yield: 87%). $^1$H NMR (CDCl$_3$, 400 MHz) δ (ppm) 8.28 (s, 2H), 7.72 (d, 2H), 7.56 (d, 2H), 7.39 (d, 2H), 7.16 (d, 2H), 2.41 (s, 3H); $^{13}$C NMR (CDCl$_3$, 100 MHz) δ (ppm) 139.1, 137.1, 130.6, 130.3, 129.7, 123.0, 121.1, 120.7, 116.3, 84.9, 20.4.

Synthesis of Intermediate G

The intermediate F (5.09 g, 10 mmol) was dissolved in THF (30 ml), and n-butyllithium (4 ml, 2.5M in hexane) was added thereto at −78°. One hour after the addition, a solution of chlorotriphenylsilane (2.95 g, 10 mmol) in THF (5 ml) was gradually added thereto at −78°. The reaction mixture was stirred at room temperature for five hours, and water was added thereto. The reaction solution was extracted three times with diethylether (30 ml). The obtained diethylether layer was dried over MgSO$_4$ and then dried under a reduced pressure to obtain a crude product. The crude product was purified by silica gel column chromatography to give an intermediate G as a white solid (3.27 g, yield: 51%). $^1$H NMR (CDCl$_3$, 400 MHz) δ (ppm) 8.61-8.54 (m, 2H), 8.24 (s, 1H), 8.16 (dd, 1H), 7.71-7.10 (m, 22H), 2.41 (s, 3H); $^{13}$C NMR (CDCl$_3$, 100 MHz) δ (ppm) 139.3, 137.2, 135.2, 134.7, 133.8, 133.0, 131.2, 130.1, 129.7, 129.4, 129.1, 127.2, 123.0, 121.3, 121.1, 120.2, 119.1, 113.0, 112.7, 82.1.

Synthesis of Intermediate H

The intermediate G (0.549 g, 0.856 mmol) and aniline (0.112 g, 1.2 mmol) were dissolved in toluene (5 ml), and t-BuONa (0.144 g, 1.5 mmol), Pd(dba)2 (0.018 g, 0.02 mmol), and (t-Bu)3P (0.004~0.006 g, 0.02~0.03 mmol) were added thereto. The reaction mixture was stirred at 80° C. for five hours. The reaction solution was extracted three times with ethylether (20 ml). The collected organic layer was dried over magnesium sulfate to evaporate the solvent. The resultant residue was purified by silica gel column chromatography to give an intermediate H (0.385 g, yield: 74%). $^1$H NMR (CDCl$_3$, 400 MHz) δ (ppm) 8.61-8.53 (m, 2H), 8.13 (dd, 1H), 7.75-6.75 (m, 27H), 6.11 (bs, 1H); $^{13}$C NMR (CDCl$_3$, 100 MHz) δ (ppm) 144.6, 140.5, 135.7, 135.1, 134.9, 133.5, 133.0, 131.7, 130.3, 129.7, 129.6, 129.3, 127.9, 124.3, 122.3, 120.7, 120.4, 119.0, 116.7, 115.9, 113.8, 111.1, 109.3, 99.7, 20.4.

Synthesis of Compound 11

The intermediate G (6.42 g, 10 mmol), the intermediate H (7.29 g, 12 mmol), t-BuONa (2.9 mg, 30 mmol), Pd$_2$(dba)$_3$ (183 mg, 0.2 mmol), and P(t-Bu)$_3$ (40 mg, 0.2 mmol) were dissolved in toluene (40 ml), and the reaction mixture was stirred at 90° C. for three hours. After the reaction was terminated, the reaction solution was cooled to room temperature and then extracted three times with distilled water and diethylether (40 ml). The collected organic layer was dried over magnesium sulfate to evaporate the solvent. The resultant residue was purified by silica gel column chromatography to give the compound 11 (8.85 g, yield: 79%). $^1$H NMR (CDCl$_3$, 400 MHz) δ (ppm) 8.76 (d, 2H), 8.44 (s, 2H), 8.12 (dd, 2H), 7.66-6.60 (m, 49H), 2.41 (s, 3H); $^{13}$C NMR (CDCl$_3$, 100 MHz) δ (ppm) 149.7, 140.1, 138.5, 135.7, 135.1, 134.9, 133.3, 132.5, 131.7, 130.3, 129.7, 129.6, 129.3, 127.9, 122.9, 122.7, 121.7, 120.7, 120.3, 117.9, 116.3, 112.8, 110.6, 108.1, 20.5.

Synthesis Example 4

Synthesis of Compound 21

A compound 21 was synthesized according to Reaction Scheme 4 below.

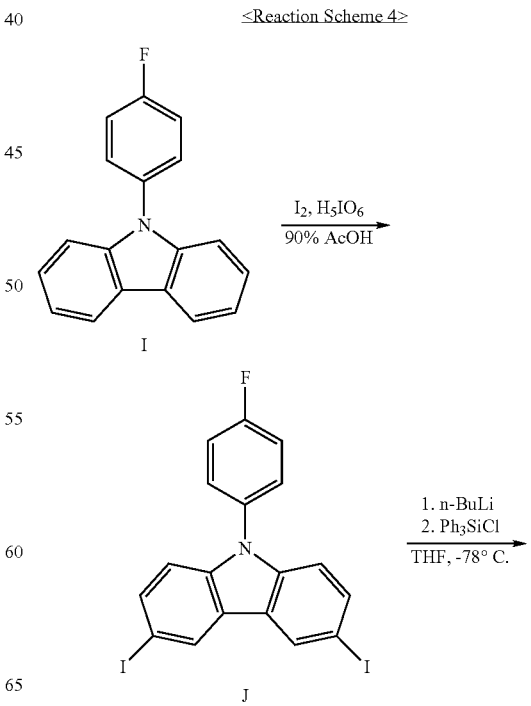

<Reaction Scheme 4>

-continued

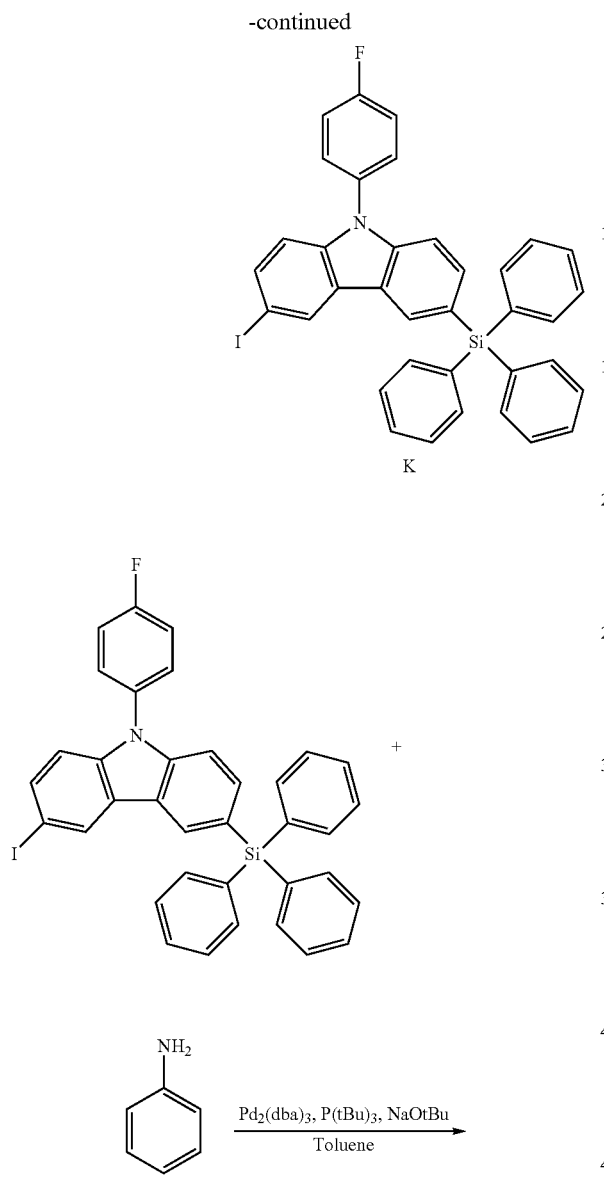

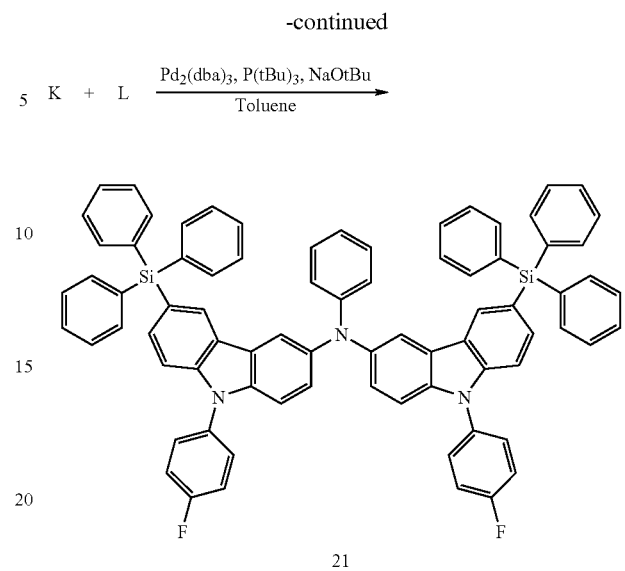

Synthesis of Intermediate I

Carbazole (16.7 g, 100 mmol), 4-fluoroiodobenzene (28.9 g, 130 mmol), CuI (1.9 g, 10 mmol), $K_2CO_3$ (138 g, 1.0 mol), and 18-crown-6 (530 mg, 2 mmol) were dissolved in DMPU (500 ml), and the reaction mixture was stirred at 170° C. for eight hours. After the reaction was terminated, the reaction solution was cooled to room temperature, and a solid material was filtered out. A trace amount of an ammonia solution was added to the filtrate, and the reaction solution was extracted three times with diethylether (300 ml). The collected diethylether layer was washed with excess distilled water, dried over $MgSO_4$, filtered, and dried under a reduced pressure to obtain a crude product. The crude product was purified by silica gel column chromatography to give an intermediate I as a white solid (23.5 g, yield: 90%). $^1$H NMR ($CDCl_3$, 400 MHz) δ (ppm) 8.11 (d, 2H), 7.54 (m, 2H), 7.34 (d, 4H), 7.24 (m, 2H), 7.06 (m, 2H); $^{13}$C NMR ($CDCl_3$, 100 MHz) δ (ppm) 158.4 (d), 139.4, 136.6, 126.3, 125.4 (d), 123.0, 120.3, 119.9, 113.5 (d), 109.6.

Synthesis of Intermediate J

The intermediate I (2.61 g, 10 mmol) was added to an 80% acetic acid (100 ml), and iodine ($I_2$) (2.714 g, 10.7 mmol) and ortho-periodinic acid ($H_5IO_6$) (0.666 g, 2.92 mmol) in a solid phase were added thereto. The reaction mixture was stirred at 80° C. under a nitrogen atmosphere for three hours. After the reaction was terminated, the reaction solution was extracted three times with ethylether (50 ml). The collected organic layer was dried over magnesium sulfate to evaporate the solvent. The resultant residue was purified by silica gel column chromatography to give an intermediate J as a white solid (4.10 g, yield: 80%). $^1$H NMR ($CDCl_3$, 400 MHz) δ (ppm) 8.28 (s, 2H), 7.72 (d, 2H), 7.56-7.52 (m, 4H), 7.08-7.03 (m, 2H); $^{13}$C NMR ($CDCl_3$, 100 MHz) δ (ppm) 158.7 (d), 138.1, 134.9, 130.6, 125.4 (d), 123.0, 121.1, 116.3, 113.4, 101.9.

Synthesis of Intermediate K

The intermediate J (5.13 g, 10 mmol) was dissolved in THF (30 ml), and n-butyllithium (4 ml, 2.5M in hexane) was added

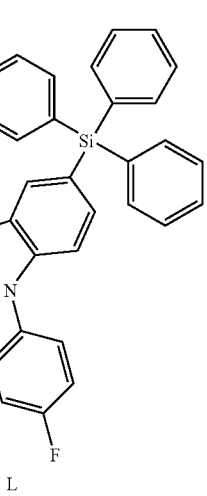

thereto at −78° C. One hour after the addition, a solution of chlorotriphenylsilane (2.95 g, 10 mmol) in THF (5 ml) was gradually added thereto at −78° C. The reaction mixture was stirred at room temperature for five hours, and water was added thereto. The reaction solution was extracted three times with diethylether (30 ml). The obtained diethylether layer was dried over MgSO$_4$ and then dried under a reduced pressure to obtain a crude product. The crude product was purified by silica gel column chromatography to give an intermediate K as a white solid (3.42 g, yield: 53%). $^1$H NMR (CDCl$_3$, 400 MHz) δ (ppm) 8.35-8.28 (m, 2H), 8.10 (s, 1H), 8.00 (dd, 1H), 7.55-6.93 (m, 22H); $^{13}$C NMR (CDCl$_3$, 100 MHz) δ (ppm) 159.1 (d), 138.8, 136.7, 135.7, 135.1, 132.8, 132.1, 131.77, 130.6, 129.6, 127.9, 125.4 (d), 123.4, 121.7, 121.6, 119.6, 113.5, 113.4, 113.3, 113.1, 102.2.

Synthesis of Intermediate L

The intermediate K (0.553 g, 0.856 mmol) and aniline (0.112 g, 1.2 mmol) were dissolved in toluene (5 ml), and t-BuONa (0.144 g, 1.5 mmol), Pd(dba)$_2$ (0.018 g, 0.02 mmol), and P(t-Bu)$_3$ (0.004~0.006 g, 0.02~0.03 mmol) were then added thereto. The reaction mixture was stirred at 80° C. for five hours. The reaction solution was extracted three times with ethylether (20 ml). The collected organic layer was dried over magnesium sulfate to evaporate the solvent. The resultant residue was purified by silica gel column chromatography to give an intermediate L (0.408 g, yield: 78%). $^1$H NMR (CDCl$_3$, 400 MHz) δ (ppm) 8.72-8.68 (m, 2H), 8.22 (dd, 1H), 7.85-6.81 (m, 27H), 6.50 (bd, 1H); $^{13}$C NMR (CDCl$_3$, 100 MHz) δ (ppm) 160.2 (d), 144.6, 139.5, 135.2, 135.0, 133.5, 132.8, 132.0, 131.7, 129.6, 129.3, 127.9, 125.4 (d), 124.3, 122.3, 120.4, 119.0, 116.7, 113.9, 113.8, 113.5, 113.3, 111.1, 109.3, 99.7.

Synthesis of Compound 21

The intermediate K (6.46 g, 10 mmol), the intermediate L (7.33 g, 12 mmol), t-BuONa (2.9 mg, 30 mmol), Pd$_2$(dba)$_3$ (183 mg, 0.2 mmol), and P(t-Bu)$_3$ (40 mg, 0.2 mmol) were dissolved in toluene (40 ml), and the reaction mixture was stirred at 90° C. for three hours. After the reaction was terminated, the reaction solution was cooled to room temperature and then extracted three times with distilled water and diethylether (40 ml). The collected organic layer was dried over magnesium sulfate to evaporate the solvent. The resultant residue was purified by silica gel column chromatography to give the compound 21 (8.46 g, yield: 75%). $^1$H NMR (CDCl$_3$, 400 MHz) δ (ppm) 8.76 (d, 2H), 8.44 (s, 2H), 8.15 (dd, 2H), 7.88-6.80 (m, 49H); $^{13}$C NMR (CDCl$_3$, 100 MHz) δ (ppm) 158.2 (d), 149.7, 140.2, 137.6, 135.3, 135.1, 133.9, 132.4, 131.7, 129.6, 129.3, 127.9, 125.4 (d), 122.9, 122.7, 121.7, 120.3, 117.9, 116.3, 113.5, 113.3, 112.8, 110.6, 108.7.

Synthesis Example 5

Synthesis of Compound 22

A compound 22 was synthesized according to Reaction Scheme 5 below.

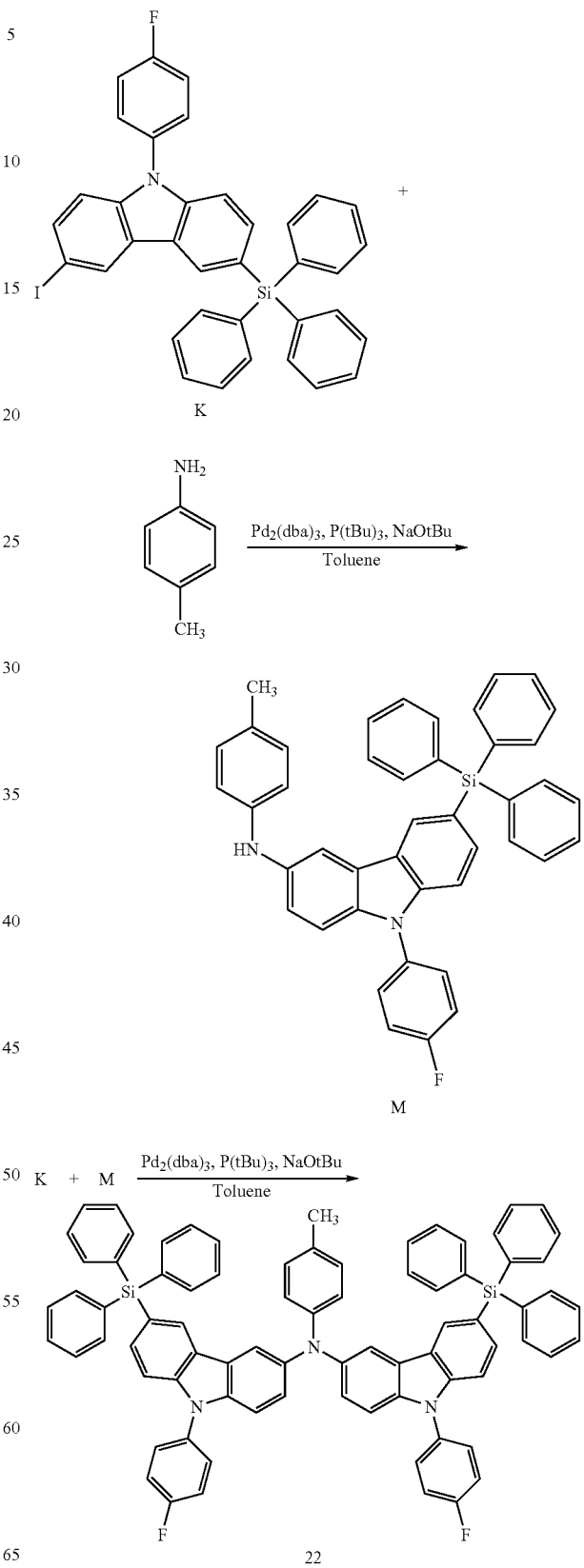

Synthesis of intermediate M

The intermediate K (0.553 g, 0.856 mmol) and p-toluidine (0.129 g, 1.2 mmol) were dissolved in toluene (5 ml), and t-BuONa (0.144 g, 1.5 mmol), Pd(dba)$_2$ (0.018 g, 0.02 mmol), and (t-Bu)$_3$P (0.004~0.006 g, 0.02~0.03 mmol) were then added thereto. The reaction mixture was stirred at 80° C. for five hours. The reaction solution was extracted three times with ethylether (20 ml). The collected organic layer was dried over magnesium sulfate to evaporate the solvent. The resultant residue was purified by silica gel column chromatography to give an intermediate M (0.371 g, yield: 81%). $^1$H NMR (CDCl$_3$, 400 MHz) δ (ppm) 8.61 (d, 1H), 8.54 (s, 1H), 8.10 (dd, 1H), 7.54-6.75 (m, 27H), 2.25 (s, 3H); $^{13}$C NMR (CDCl$_3$, 100 MHz) δ (ppm) 159.3 (d), 139.7 (d), 135.2, 135.1, 133.4, 132.8, 132.0, 131.7, 129.6, 129.5, 127.9, 125.4 (d), 124.4, 122.7, 120.2, 118.5, 115.9, 118.6, 115.9, 113.8, 111.1, 109.3, 99.7, 20.3.

Synthesis of compound 22

The intermediate K (6.46 g, 10 mmol), the intermediate M (7.50 g, 12 mmol), t-BuONa (2.9 mg, 30 mmol), Pd$_2$(dba)$_3$ (183 mg, 0.2 mmol), and P(t-Bu)$_3$ (40 mg, 0.2 mmol) were dissolved in toluene (40 ml), and the reaction mixture was stirred at 90° C. for three hours. After the reaction was terminated, the reaction solution was cooled to room temperature and then extracted three times with distilled water and diethylether (40 ml). The collected organic layer was dried over magnesium sulfate to evaporate the solvent. The resultant residue was purified by silica gel column chromatography to give the compound 22 (9.14 g, yield: 80%). $^1$H NMR (CDCl$_3$, 400 MHz) δ (ppm) 8.94 (d, 2H), 8.53 (s, 1H), 8.22 (dd, 2H), 7.83-6.53 (m, 48H), 2.23 (s, 3H); $^{13}$C NMR (CDCl$_3$, 100 MHz) δ (ppm) 160.2 (d), 149.2, 140.2, 137.6, 136.5, 135.5, 133.3, 132.2, 131.9, 131.5, 129.6, 129.4, 128.8, 127.6, 125.2 (d), 121.7, 120.3, 117.9, 116.3, 113.5, 113.3, 112.8, 110.6, 108.6, 21.1.

Example 1

A 15 Ω/cm$^2$ ITO glass substrate (Corning, 1,200 Å) was cut into pieces of 50 mm×50 mm×0.7 mm in size, followed by ultrasonic cleaning in isopropyl alcohol and pure water (5 minutes for each), exposure to UV light for 30 minutes, and then ozone cleaning, to thereby form anodes. The anodes were placed in a vacuum deposition machine.

Compound 1 was vacuum-deposited to a thickness of 600 Å on the anodes to form hole injection layers. Then, a hole transport compound, 4,4'-bis[N-(1-naphthyl)-N-phenylamino]biphenyl (NPB) was vacuum-deposited to a thickness of 300 Å on the hole injection layers to form hole transport layers.

A known blue fluorescent host, IDE215 (Idemitsu), and a known blue fluorescent dopant, IDE118 (Idemitsu) (weight ratio of 98:2) were co-deposited to a thickness of 200 Å on the hole transport layers to form emitting layers.

Next, Alq$_3$ was deposited to a thickness of 300 Å on the emitting layers to form electron transport layers. LiF (10 Å, electron injection layers), which was halogenated alkaline metal, and Al (3,000 Å, cathodes) were vacuum-deposited on the electron transport layers to form LiF/Al electrodes, thereby completing organic light-emitting devices.

The organic light-emitting devices exhibited a driving voltage of 7.24 V at a current density of 100 mA/cm$^2$, high brightness of 6,945 cd/m$^2$, color coordinates of (0.143, 0.243), and an emission efficiency of 6.95 cd/A.

Example 2

Organic light-emitting devices were manufactured in the same manner as in Example 1 except that hole injection layers were formed using compound 4 instead of compound 1.

The organic light-emitting devices exhibited a driving voltage of 7.31 V at a current density of 100 mA/cm$^2$, high brightness of 6,465 cd/m$^2$, color coordinates of (0.143, 0.241), and an emission efficiency of 6.47 cd/A.

Comparative Example 1

Organic light-emitting devices were manufactured in the same manner as in Example 1 except that hole injection layers were formed using IDE406 (Idemitsu) instead of compound 1.

The organic light-emitting devices exhibited a driving voltage of 7.75 V at a current density of 100 mA/cm$^2$, brightness of 6,219 cd/m$^2$, color coordinates of (0.143, 0.243), and emission efficiency of 6.22 cd/A.

When comparing the organic light-emitting devices employing the compounds of Formula 1 according to aspects of the present invention and the known IDE406 as hole injection layer materials, all the organic light-emitting devices employing the compounds of Formula 1 exhibited good I-V-L characteristics which were greater than or equal to those of the organic light-emitting devices employing IDE406. The organic light-emitting devices employing the compounds of Formula 1 according to aspects of the present invention also exhibited a low driving voltage, high efficiency, and high brightness, by virtue of good hole injection and transport capabilities of the compounds of Formula 1.

As descried above, a silanylamine-based compound of Formula 1 has good electrical characteristics and charge transport capability, and thus, is useful as a hole injection material, a hole transport material, and/or an emitting material for fluorescent or phosphorescent devices capable of producing light of a full spectrum of colors, including red, green, blue, and white. Thus, the silanylamine-based compound can be used to produce an organic light-emitting device with high efficiency, a low driving voltage, and high brightness.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A silanylamine-based compound represented by Formula 1 below:

<Formula 1>

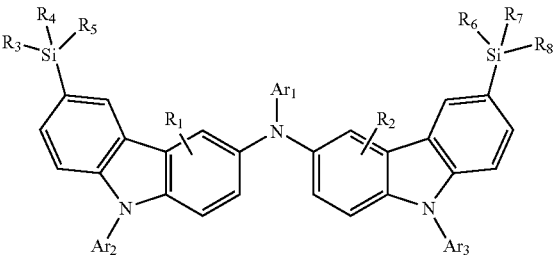

wherein,

R₁, R₂, R₃, R₄, R₅, R₆, R₇, and R₈ are each independently hydrogen, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_5$-$C_{30}$ aryloxy group, a substituted or unsubstituted $C_5$-$C_{30}$ aryl group, or a substituted or unsubstituted $C_2$-$C_{30}$ heteroaryl group, and adjacent groups selected from R₃, R₄, R₅, R₆, R₇, and R₈ may optionally join together to form a saturated or unsaturated carbon ring; and Ar₁, Ar₂, and Ar₃ are each independently hydrogen, a substituted or unsubstituted $C_5$-$C_{30}$ aryl group, or a substituted or unsubstituted $C_2$-$C_{30}$ heteroaryl group.

2. The silanylamine-based compound of claim 1, wherein Ar₁, Ar₂, and Ar₃ are each independently a substituted or unsubstituted $C_5$-$C_{12}$ aryl group or a substituted or unsubstituted $C_3$-$C_{15}$ heteroaryl group.

3. The silanylamine-based compound of claim 1, wherein Ar₁, Ar₂, and Ar₃ are each independently a phenyl group, a $C_1$-$C_5$ alkylphenyl group, a $C_1$-$C_5$ alkoxyphenyl group, a cyanophenyl group, a phenoxyphenyl group, a halophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkylcarbazolyl group, a biphenyl group, a $C_1$-$C_5$ alkylbiphenyl group, a $C_1$-$C_5$ alkoxybiphenyl group, or a pyridyl group.

4. The silanylamine-based compound of claim 1, wherein Ar₁, Ar₂, and Ar₃ are each independently a fluorenyl group, a carbazolyl group, a phenyl group, a naphthyl group, a biphenyl group, or an aryl group that is substituted by one, two, or three selected from the group consisting of $C_1$-$C_3$ alkyl, $C_1$-$C_3$ alkoxy, cyano, phenoxy, phenyl, and halogen.

5. The silanylamine-based compound of claim 1, wherein Ar₁, Ar₂, and Ar₃ are each independently selected from the group consisting of a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, and p-tolyl group, a mesityl group, a phenoxyphenyl group, a (α,α-dimethylbenzene) phenyl group, a (N,N'-dimethyl)aminophenyl group, a (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinolyl group, a phenanthryl group, a triphenylene group, a pentaphenyl group, a hexaphenyl group, and a carbazolyl group.

6. The silanylamine-based compound of claim 1, wherein R₁, R₂, R₃, R₄, R₅, R₆, R₇, and R₈ are each independently a substituted or unsubstituted $C_1$-$C_{10}$ alkyl group, a substituted or unsubstituted $C_1$-$C_{10}$ alkoxy group, a substituted or unsubstituted $C_6$-$C_{12}$ aryl group, a substituted or unsubstituted $C_6$-$C_{12}$ aryloxy group, or a $C_3$-$C_{12}$ heteroaryl group.

7. The silanylamine-based compound of claim 1, wherein R₁, R₂, R₃, R₄, R₅, R₆, R₇, and R₈ are each independently a $C_1$-$C_{10}$ alkyl group, a phenyl group, a halophenyl group, a cyanophenyl group, a $C_1$-$C_{10}$ alkylphenyl group, a $C_1$-$C_{10}$ alkoxyphenyl group, a biphenyl group, a halobiphenyl group, a naphthyl group, a halonaphthyl group, a $C_1$-$C_{10}$ alkylnaphthyl group, or a $C_1$-$C_{10}$ alkoxynaphthyl group.

8. The silanylamine-based compound of claim 1, which is a compound 1, 4, 11, 21, or 22 below:

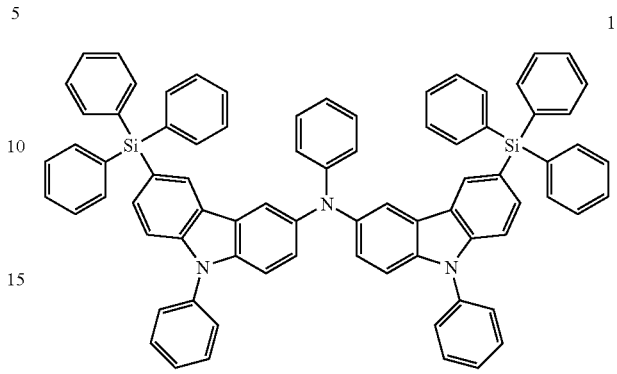

1

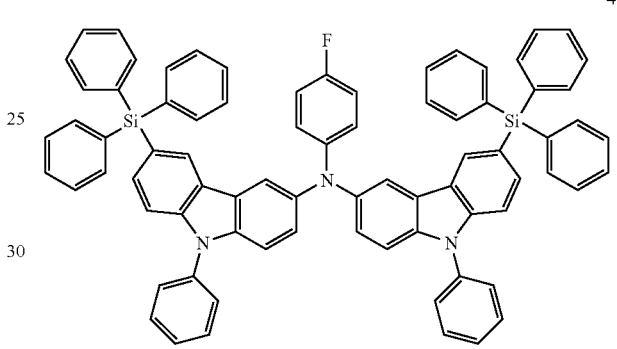

4

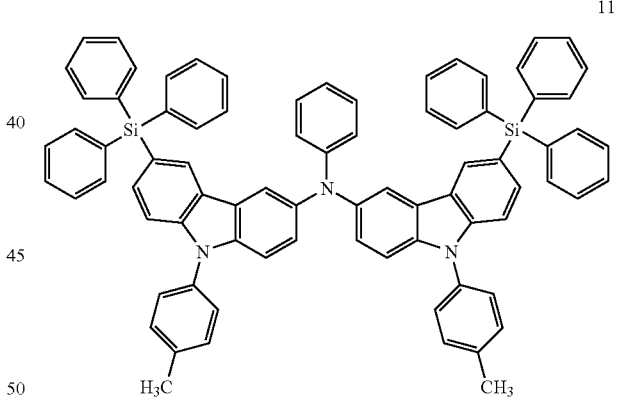

11

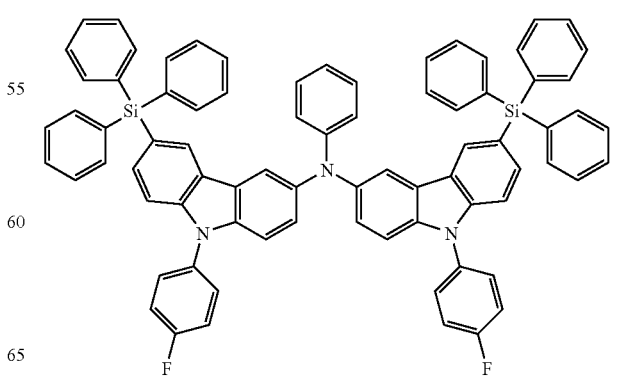

21

-continued

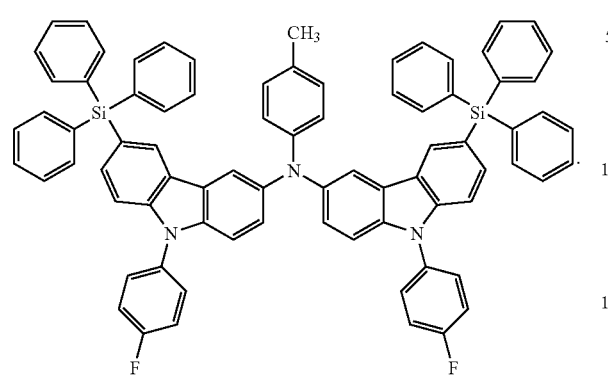

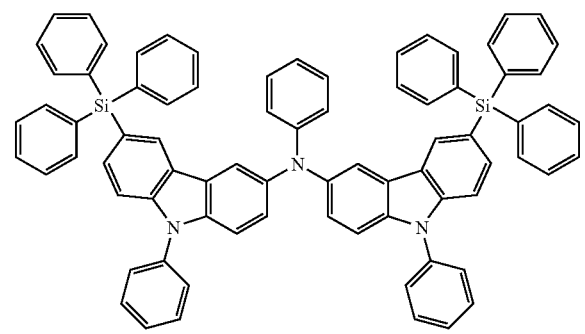

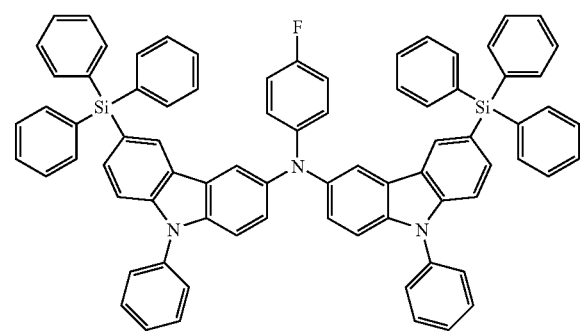

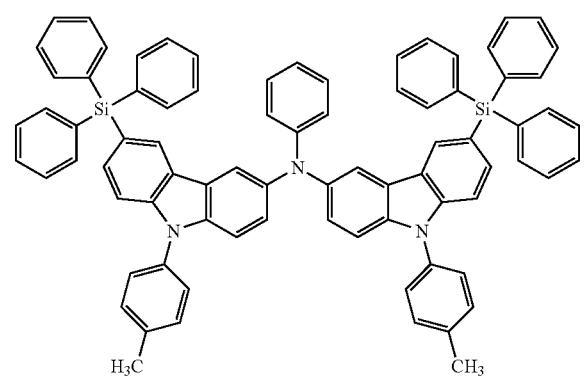

-continued

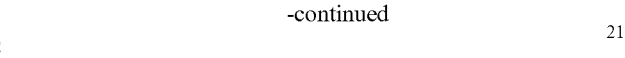

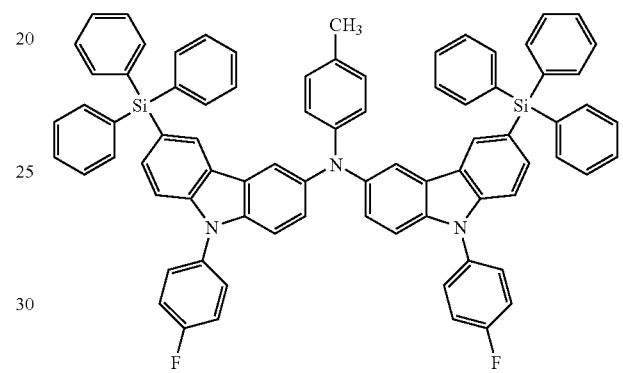

9. An organic light-emitting device comprising:
   a first electrode;
   a second electrode; and
   one or more organic layers interposed between the first electrode and the second electrode, wherein at least one of the one or more organic layers comprises the silanylamine-based compound of claim 1.

10. The organic light-emitting device of claim 9, wherein the organic layer comprising the silanylamine-based compound is a hole injection layer or a hole transport layer.

11. The organic light-emitting device of claim 9, wherein the organic layer comprising the silanylamine-based compound is a single layer having hole injection capability and hole transport capability.

12. The organic light-emitting device of claim 10, wherein the organic light-emitting device has one of the following structures:
   first electrode/hole injection layer/emitting layer/second electrode;
   first electrode/hole injection layer/hole transport layer/emitting layer/electron transport layer/second electrode; or
   first electrode/hole injection layer/hole transport layer/emitting layer/electron transport layer/electron injection layer/second electrode structure.

13. The organic light-emitting device of claim 12, further comprising at least one of a hole blocking layer and an electron blocking layer.

14. The organic light-emitting device of claim 11, wherein the organic light-emitting device has one of the following structures:

first electrode/single layer having hole injection capability and hole transport capability/emitting layer/electron transport layer/second electrode or first electrode/single layer having hole injection capability and hole transport capability/emitting layer/electron transport layer/electron injection layer/second electrode.

15. The organic light-emitting device of claim 14, further comprising at least one of a hole blocking layer and an electron blocking layer.

16. The organic light-emitting device of claim 9, wherein the organic layer comprising the silanylamine-based compound is an emitting layer.

17. The organic light-emitting device of claim 16, wherein the emitting layer further comprises a phosphorescent or fluorescent material.

18. The organic light-emitting device of claim 9, wherein $Ar_1$, $Ar_2$, and $Ar_3$ are each independently a substituted or unsubstituted $C_5$-$C_{12}$ aryl group or a substituted or unsubstituted $C_3$-$C_{15}$ heteroaryl group.

19. The organic light-emitting device of claim 9, wherein $Ar_1$, $Ar_2$, and $Ar_3$ are each independently a phenyl group, a $C_1$-$C_5$ alkylphenyl group, a $C_1$-$C_5$ alkoxyphenyl group, a cyanophenyl group, a phenoxyphenyl group, a halophenyl group, a naphthyl group, a $C_1$-$C_5$ alkylnaphthyl group, a $C_1$-$C_5$ alkoxynaphthyl group, a cyanonaphthyl group, a halonaphthyl group, a fluorenyl group, a carbazolyl group, a $C_1$-$C_5$ alkylcarbazolyl group, a biphenyl group, a $C_1$-$C_5$ alkylbiphenyl group, a $C_1$-$C_5$ alkoxybiphenyl group, or a pyridyl group.

20. The organic light-emitting device of claim 9, wherein $Ar_1$, $Ar_2$, and $Ar_3$ are each independently a fluorenyl group, a carbazolyl group, a phenyl group, a naphthyl group, a biphenyl group, or an aryl group that is substituted by one, two, or three selected from the group consisting of $C_1$-$C_3$ alkyl, $C_1$-$C_3$ alkoxy, cyano, phenoxy, phenyl, and halogen.

21. The organic light-emitting device of claim 9, wherein $Ar_1$, $Ar_2$, and $Ar_3$ are each independently selected from the group consisting of a phenyl group, an ethylphenyl group, an ethylbiphenyl group, an o-, m-, or p-fluorophenyl group, a dichlorophenyl group, a dicyanophenyl group, a trifluoromethoxyphenyl group, an o-, m-, and p-tolyl group, a mesityl group, a phenoxyphenyl group, a ($\alpha,\alpha$-dimethylbenzene) phenyl group, a (N,N'-dimethyl)aminophenyl group, a (N,N'-diphenyl)aminophenyl group, a pentalenyl group, a naphthyl group, a methylnaphthyl group, an anthracenyl group, an azulenyl group, a heptalenyl group, an acenaphthylenyl group, a fluorenyl group, an anthraquinolyl group, a phenanthryl group, a triphenylene group, a pentaphenyl group, a hexaphenyl group, and a carbazolyl group.

22. The organic light-emitting device of claim 9, wherein $R_1$, $R_2$, $R_3$, $R_4$, $R_5$, $R_6$, $R_7$, and $R_8$ are each independently a substituted or unsubstituted $C_1$-$C_{10}$ alkyl group, a substituted or unsubstituted $C_1$-$C_{10}$ alkoxy group, a substituted or unsubstituted $C_6$-$C_{12}$ aryl group, a substituted or unsubstituted $C_6$-$C_{12}$ aryloxy group, or a $C_3$-$C_{12}$ heteroaryl group.

23. The organic light-emitting device of claim 9, wherein $R_1$, $R_2$, $R_3$, $R_4$, $R_5$, $R_6$, $R_7$, and $R_8$ are each independently a $C_1$-$C_{10}$ alkyl group, a phenyl group, a halophenyl group, a cyanophenyl group, a $C_1$-$C_{10}$ alkylphenyl group, a $C_1$-$C_{10}$ alkoxyphenyl group, a biphenyl group, a halobiphenyl group, a naphthyl group, a halonaphthyl group, a $C_1$-$C_{10}$ alkylnaphthyl group, or a $C_1$-$C_{10}$ alkoxynaphthyl group.

24. The organic light-emitting device of claim 9, wherein the silanylamine-based compound is which is a compound 1, 4, 11, 21, or 22 below:

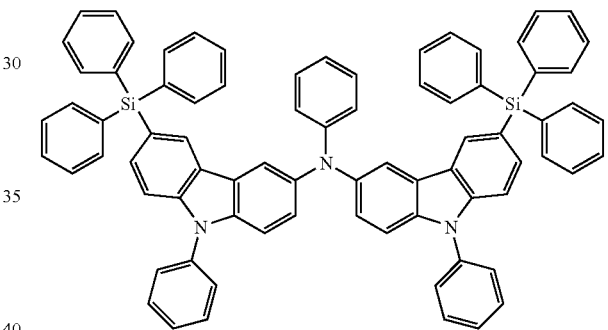

1

* * * * *

UNITED STATES PATENT AND TRADEMARK OFFICE
CERTIFICATE OF CORRECTION

PATENT NO.       : 7,754,349 B2
APPLICATION NO.  : 11/947985
DATED            : July 13, 2010
INVENTOR(S)      : Yoon-Hyun Kwak et al.

It is certified that error appears in the above-identified patent and that said Letters Patent is hereby corrected as shown below:

Column 44-46, line 24, delete formulas 1, 4, 11, 21 and 22:

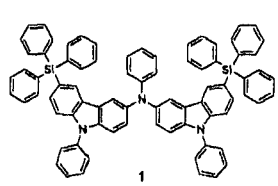
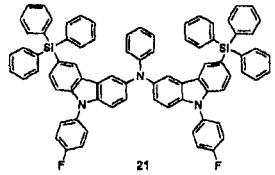
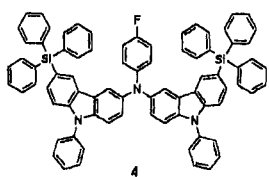
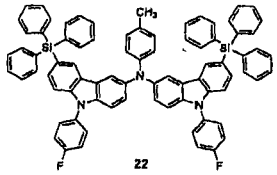
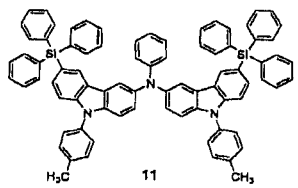

"                                          ".

Column 48, line 24, insert formulas 4, 11, 21 and 22 after formula 1.

Signed and Sealed this

Thirtieth Day of November, 2010

David J. Kappos
*Director of the United States Patent and Trademark Office*